(12) United States Patent
Wang et al.

(10) Patent No.: US 12,221,598 B2
(45) Date of Patent: Feb. 11, 2025

(54) FULL-AUTOMATIC CELL PRODUCTION LINE

(71) Applicant: HELP THERAPEUTICS CO., LTD., Jiangsu (CN)

(72) Inventors: Jiaxian Wang, Jiangsu (CN); Hang Zhang, Jiangsu (CN); Yanan Zhou, Jiangsu (CN); Xiaojuan Shi, Jiangsu (CN); Qian Wang, Jiangsu (CN)

( * ) Notice: Subject to any disclaimer, the term of this patent is extended or adjusted under 35 U.S.C. 154(b) by 10 days.

(21) Appl. No.: 18/038,015

(22) PCT Filed: Jun. 30, 2021

(86) PCT No.: PCT/CN2021/103848
§ 371 (c)(1),
(2) Date: May 20, 2023

(87) PCT Pub. No.: WO2022/252325
PCT Pub. Date: Dec. 8, 2022

(65) Prior Publication Data
US 2023/0399600 A1  Dec. 14, 2023

(30) Foreign Application Priority Data
Jun. 3, 2021 (CN) .......................... 202110616721.5

(51) Int. Cl.
*C12M 1/00* (2006.01)
*C12M 1/12* (2006.01)
(Continued)

(52) U.S. Cl.
CPC ............ *C12M 27/16* (2013.01); *C12M 23/14* (2013.01); *C12M 23/48* (2013.01); *C12M 29/26* (2013.01);
(Continued)

(58) Field of Classification Search
CPC ...... C12M 27/16; C12M 23/14; C12M 23/48; C12M 29/26; C12M 33/04; C12M 33/10;
(Continued)

(56) References Cited

U.S. PATENT DOCUMENTS

| | | |
|---|---|---|
| 2008/0090288 A1 | 4/2008 | Hibino |
| 2017/0130189 A1 | 5/2017 | Sakamoto |
| 2020/0025782 A1 | 1/2020 | Ahlfors |

FOREIGN PATENT DOCUMENTS

| | | |
|---|---|---|
| CN | 106701576 A | 5/2017 |
| CN | 107177543 A | 9/2017 |

(Continued)

OTHER PUBLICATIONS

International Search Report for PCT/CN2021/103848 mailed Mar. 3, 2022, ISA/CN.
The Korean 1st Office Action issued on Oct. 13, 2023 for KR10-2023-7018240.
The Japanese 1st Office Action issued on Oct. 10, 2023 for JP2023-530776.

*Primary Examiner* — Liban M Hassan

(57) ABSTRACT

The present invention provides a full-automatic cell production line, comprising a culture region and an operation region. The culture region comprises a B-stage platform body, and the B-stage platform body comprises a culture area, a refrigeration area, and a robot provided with a motion track. The motion track of the robot is linearly arranged. The culture area, the refrigeration area, and a manual delivery window all surround the track, and are all located in the operation region of the robot. The operation region is integrated with a liquid storage table, a cell factory liquid changing device, and a centrifugal bottle liquid changing device. The delivery window is used between the culture region and the operation region to deliver a material. The technical solution of the present invention is mainly used for full-automatic batch production of cells.

14 Claims, 17 Drawing Sheets

(51) Int. Cl.
*C12M 1/26* (2006.01)
*C12M 1/36* (2006.01)
*C12M 3/00* (2006.01)
*C12M 3/06* (2006.01)

(52) U.S. Cl.
CPC ............ *C12M 33/04* (2013.01); *C12M 33/10* (2013.01); *C12M 37/04* (2013.01); *C12M 41/48* (2013.01)

(58) Field of Classification Search
CPC ...... C12M 37/04; C12M 41/48; C12M 23/06; C12M 23/52; C12M 29/00; C12M 33/08; C12M 37/00; C12M 41/00; A01N 1/0284; B04B 9/08; B04B 9/10
See application file for complete search history.

(56) References Cited

FOREIGN PATENT DOCUMENTS

| | | |
|---|---|---|
| CN | 207738760 U | 8/2018 |
| CN | 109251861 A | 1/2019 |
| CN | 109294890 A | 2/2019 |
| CN | 110129192 A | 8/2019 |
| CN | 110747115 A | 2/2020 |
| CN | 210974703 U | 7/2020 |
| KR | 20060027356 A | 3/2006 |
| KR | 20170026488 A | 3/2017 |
| KR | 20190039081 A | 4/2019 |

FULL-AUTOMATIC CELL PRODUCTION LINE

This application is a US National Phase application based upon PCT Application No. PCT/CN2021/103848 filed Jun. 30, 2021, which claims priority to Chinese Patent Application No. 202110616721.5, titled "FULL-AUTOMATIC CELL PRODUCTION LINE", filed on Jun. 3, 2021 with the China National Intellectual Property Administration, which is incorporated herein by reference in its entirety.

FIELD

The present application relates to the technical field of biology, and in particular to a full-automatic cell production line.

BACKGROUND

Adherent cells adhere to the surface of the culture dish during culture and continue to proliferate until the cells spread over the entire surface of the Cell Factory, at this time, the cells in the Cell Factory could be digested and collected. After centrifugation, shaking, separation, freezing and aliquoting, the cell production process is completed.

Currently, the cell culture process is manually operated, after filling the culture medium and the cells into the Cell Factory, the Cell Factory is placed into the incubator for culturing. After a period of culturing, the waste fluid of cell metabolism in the Cell Factory needs to be removed and then new culture medium is added. The process of cell passaging and freezing is also manually operated. After digestion and collection, centrifugation, shaking, separation, freezing and aliquoting are performed, which are also manually operated.

The whole process is manually operated, the efficiency is low, the operation is unstable, continuous manual working time is long, and it is difficult to improve the output.

Therefore, a new solution is required, to realize unmanned operation of cell production, to reduce the risk of contamination, improve the efficiency and reduce the costs.

SUMMARY

An object of the present invention is to provide a full-automatic cell production line for full-automatic batch production of cells.

In order to achieve the above object, the following technical solutions are provided according to the present invention.

A full-automatic cell production line includes a culture region and an operation region; where the culture region includes a B-level platform body, the B-level platform body includes a culture area, a refrigeration area and a robot equipped with a motion track; the motion track of the robot is arranged at a bottom of the B-level platform body in a linear manner; the culture area and the refrigeration area are arranged around the motion track and are both located in an operation area of the robot;

the operation region is provided with a liquid storage table, a Cell Factory liquid exchange device, a centrifugal bottle liquid exchange device and a mechanical arm in an integrated manner; the liquid storage table, the Cell Factory liquid exchange device and the centrifugal bottle liquid exchange device are arranged around the mechanical arm in the operation region and are located within a control range of the mechanical arm;

a transfer window is configured to transfer materials between the culture region and the operation region, the transfer window has a transfer turnplate and a transfer turnplate drive mechanism; the transfer turnplate has a zero position for the robot of the culture region to pick up and place the materials, and a working position for the mechanical arm of the operation region to pick up and place the materials; the transfer turnplate is configured to be driven by the transfer turnplate drive mechanism to rotate, to achieve switching between the zero position and the working position.

Preferably, a waste liquid collection device and a pipe switching device are integrated at the liquid storage table; a discharge pipeline and a sterilization pipeline of the waste liquid collection device are integrated at the waste liquid collection device; the pipe switching device includes a sterilization pipeline of the liquid storage table, and the sterilization pipeline of the liquid storage table is in communication with the sterilization pipeline of the waste liquid collection device; and a Cell Factory liquid storage device, a Cell Factory liquid removing device, a Cell Factory liquid adding device and a sterilization pipeline of the Cell Factory liquid exchange device are integrated at the Cell Factory liquid exchange device;

a centrifuge bottle liquid storage device, a centrifuge bottle liquid removing device, a centrifuge bottle liquid adding device, and a sterilization pipeline of the centrifuge bottle liquid exchange device are integrated at the centrifuge bottle liquid exchange device; and where in a case that the Cell Factory liquid adding device is in communication with the Cell Factory liquid storage device, a buffer solution is stored in the Cell Factory liquid storage device, the sterilization pipeline of the Cell Factory liquid exchange device is in communication with the Cell Factory liquid adding device and the Cell Factory liquid removing device, and the Cell Factory liquid removing device is in communication with the discharge pipeline of the waste liquid collection device via the discharge pipeline, a washing passage of the Cell Factory liquid exchange device is formed;

in a case that the Cell Factory liquid adding device is in communication with an external high-temperature sterilization source, the sterilization pipeline of the Cell Factory liquid exchange device is in communication with the Cell Factory liquid adding device and the Cell Factory liquid removing device, the Cell Factory liquid removing device is in communication with the sterilization pipeline of the waste liquid collection device, and the sterilization pipeline of the liquid storage table is in communication with an external sterilization condensing pipeline, a sterilization passage of the Cell Factory liquid exchange device is formed;

in a case that the centrifuge bottle liquid adding device is in communication with the centrifuge bottle liquid storage device, a buffer solution is stored in the centrifuge bottle liquid storage device, the sterilization pipeline of the centrifuge bottle liquid exchange device is in communication with the centrifuge bottle liquid adding device and the centrifuge bottle liquid removing device, and the centrifuge bottle liquid removing device is in communication with the discharge pipeline of the waste liquid collection device, a washing passage of the centrifuge bottle liquid exchange device is formed; and in a case that the Cell Factory liquid adding device is in communication with the external high-temperature sterilization source, the sterilization pipeline of the Cell Factory liquid exchange device is in communication with Cell Factory liquid adding device and the Cell Factory liquid removing device, the Cell Factory liquid removing device is in communication with the sterilization pipeline of the waste liquid collection device, the sterilization pipeline of the liquid storage table is in communication with the centrifuge bottle liquid adding device, the centrifuge bottle liquid adding device is in communication with the centrifuge bottle liquid removing device via the sterilization pipeline of the centrifuge bottle liquid exchange device, and the centrifuge bottle liquid removing device is in communication with the external sterilization condensing pipeline, a combined sterilization passage is formed.

Preferably, a sterilization pipeline locking structure is arranged at the liquid storage table, and the sterilization pipeline locking structure includes a stepper motor and a rocker-slider structure; where the rocker-slider structure includes:
  a slider, where the slider includes a locking slot configured to lock the sterilization pipeline of the liquid storage table;
  a slideway, where the slideway is configured to allow the slider to slide on along a preset route; and
  a two-bar linkage, where one end of the two-bar linkage is configured to be driven by the stepper motor, another end of the two-bar linkage is configured to drive, under driving of the stepper motor, the slider to slide along the slideway; and
  the sterilization pipeline of the liquid storage table is located on a motion path of the locking slot of the slider.

Preferably, switching between the washing passage and the sterilization passage is performed by a pipeline switching device;
  the pipeline switching device includes an external support, and a switching device drive mechanism and a reversing mechanism both supported by the external support; where
  the external support is provided with a guide protrusion;
  the switching device drive mechanism includes a drive motor provided with a protruding element in a fixed manner, rotation output of the drive motor is performed by a gear shaft;
  the reversing mechanism has a driven shaft, a pipe switching joint is fixed at a beginning end of the driven shaft through a bracket, and the bracket is allowed to rotate with respect to the driven shaft under an action of an external force; a follower disk, a gear disk and a guide rod are sequentially arranged at a shaft body section of the driven shaft; the follower disk is connected to the drive motor; the follower disk is located below the protruding element; the gear disk and the gear shaft are in gear transmission; an outer surface the guide rod is provided with a helical groove configured for the guide protrusion to slide in; a beginning end of the helical groove has a beginning horizontal segment, and a tail end of the helical groove has a tail horizontal segment.

Preferably, the liquid exchange device is provided with a cap twisting device in an integrated manner, the liquid exchange device is the Cell Factory liquid exchange device or the centrifuge bottle liquid exchange device; where the cap twisting device includes a cap twisting mechanism and a clamping jaw control mechanism, and the cap twisting mechanism includes:
  a cap twisting main shaft configured to rotate around its own axis; and
  a clamping jaw set mounted at an end of the cap twisting main shaft, where the clamping jaw set includes a clamping jaw limiting component and a plurality of clamping jaws; and where the clamping jaw limiting component includes a plurality of elastic rings; each of the clamping jaws includes a clamping portion, a mounting pivot connected to the cap twisting main shaft and a limiting structure arranged in sequence; the limiting structure corresponds to the cap twisting main shaft, one side of the limiting structure facing the cap twisting main shaft has a slope surface structure, and the slope surface structure is a inclined surface structure inclined toward the cap twisting main shaft; and the slope surface structures of the clamping jaws of the clamping jaw set together form a cavity approximate to a circular truncated cone; and where
  each of the plurality of elastic rings is sleeved on another side of the limiting structure of each of the plurality of clamping jaws of the clamping jaw set; the clamping jaw control mechanism includes a clamping jaw control shaft coaxially arranged with the cap twisting main shaft, where the clamping jaw control shaft is allowed to move along its own axial direction; an end of the clamping jaw control shaft is provided with a control terminal, where the control terminal is located in the cavity approximate to the circular truncated cone, in a case that a position of the control terminal with respect to the cavity approximate to the circular truncated cone is changed, a rotation angle of the mounting pivot of the clamping jaw is changed, and an opening degree of the clamping jaw set is also changed.

Preferably, the liquid storage table is further provided with a liquid storage bag shaking device and a liquid storage bag weighing device in an integrated manner, the liquid storage bag weighing device is located above the waste liquid collection device, and the liquid storage bag shaking device is located above the liquid storage bag weighing device; and where
  the liquid storage bag shaking device includes a shaker drive mechanism and a storage bag box driven by the shaker drive mechanism and configured for storing a storage bag; the shaker drive mechanism and the storage bag box are drivably connected in a detachable manner.

Preferably, the operation region is provided with a full-automatic centrifuge in an integrated manner, where the full-automatic centrifuge includes a drive mechanism and a rotation mechanism, the drive mechanism is configured to provide a driving force, and the rotation mechanism is configured to be driven by the driving force, to rotate around an axis of a drive shaft of the drive mechanism; and where the rotation mechanism includes:
  a horizontal rotor configured to rotate around the axis of the drive shaft, and the horizontal rotor has a plurality of arms of force extending in a radial direction by taking the axis as a starting point; an end of the each of the plurality of arms of force is provided with a first arm of force component and a second arm of force component, and a clamping portion is formed by the first arm of force component of an end of one of the plurality of arms of force and the second arm of force component of an end of an arm of force adjacent to the one of the plurality of arms of force;

a plurality of swinging buckets, where each of the swinging buckets includes an annular wall and a bottom wall obliquely extending along a direction of the axis by taking a bottom circle of the annular wall as a starting point; and an upper end of the annular wall is mounted at the clamping portion; and the drive mechanism includes a servo motor, the servo motor is provided with a zero-position switch, and an output shaft of the servo motor is connected to the drive shaft.

Preferably, the full-automatic centrifuge further includes a plurality of optical fiber detection switches arranged to surround the swinging buckets in one-to-one correspondence; where each of the optical fiber detection switches includes a signal emission unit configured to emit a signal in a direction parallel to a plane where the rotation mechanism is located, and a signal reception unit configured to receive the signal which is reflected; and where in a case that an emitted signal corresponds to the swinging bucket, the swinging bucket is provided with a hole in a signal travelling path of the optical fiber detection switch, and the signal reception unit is configured to receive the signal reflected by a wall of a centrifuge container or a wall of the swinging bucket; and in a case that the emitted signal passes below the swinging bucket, the signal reception unit is configured to receive the signal reflected by the wall of a centrifuge container or a wall of the drive shaft.

Preferably, the operation region further includes an automatic cryogenic vial opening and aliquoting device, the automatic cryogenic vial opening and aliquoting device includes a cap screwing main shaft, liquid adding device and liquid adding main shaft, where the liquid adding device and the liquid adding main shaft are in communication with each other via a liquid removing peristaltic pump when liquid adding is performed to a cryogenic vial;

the cap screwing main shaft includes a lifting module for cap screwing and a fixing platform, where the lifting module for cap screwing includes a guide rail, a slider and a motor, the slider is drivably connected to the motor and is configured to move along the guide rail, and the fixing platform is mounted at the slider and is allowed to move along with the slider;

a vial cap detection device, a vial body detection device, a cap screwing servo motor, and a vial cap detaching device are mounted on the fixing platform, where the vial cap detection device is embodied as a plurality of reflective laser sensors, the vial body detection device is a single reflective laser sensor, and the cap screwing servo motor is embodied as a set of a plurality of servo motors respectively connected to the vial cap detaching device;

the liquid adding device includes a liquid adding platform, a sterilization platform and a centrifuge bottle weighing platform, where the liquid adding platform and the sterilization platform are arranged in parallel, an upper end of the centrifuge bottle weighing platform is provided with a centrifuge bottle placing table, the liquid adding platform or the sterilization platform is provided with a liquid removing double-needle, the sterilization platform is provided with a pushrod locking device, and the pushrod locking device is configured to move axially to be correspondingly clamped with an upper structure of the liquid removing double-needle, to achieve fixation;

the liquid adding main shaft includes a lifting module for liquid adding, a translation module for liquid adding, a basic plate and a liquid adding needle, where the liquid adding needle is fixed at the basic plate, the lifting module for liquid adding and the translation module for liquid adding are driven by a motor and a screw rod; the translation module for liquid adding is provided with a sliding plate, the lifting module for liquid adding is provided with a guide rail, and the translation module for liquid adding is allowed to move on the lifting module for liquid adding through cooperation between the sliding plate and the guide rail; and the basic plate is arranged at the translation module for liquid adding.

Preferably, the vial cap detaching device includes a spring, a guide pipe provided with L-shaped movement openings at two surfaces, a slider moving pipe and a casing pipe mounting plate; where an inner side of a lower end of the guide pipe is provided with threads configured to be engaged with a vial cap of the cryogenic vial, the guide pipe is arranged at an outer periphery of the slider moving pipe; the spring is sleeved at an outer periphery of the guide pipe in a clamped manner; and the two surfaces of the guide pipe provided with the L-shaped movement openings are opposite to each other;

the slider moving pipe is provided with two protrusions, and the protrusions are configured to move, under an action of a driving force, in the L-shaped movement openings in the surfaces of the guide pipe;

a rotation shaft is arranged inside the slider moving pipe, the rotation shaft has one end connected to the vial cap and another end connected to the casing pipe mounting plate; and the casing pipe mounting plate is connected to the cap screwing servo motor; and where in a case that the cap screwing servo motor drives, via the rotation shaft, the protrusions to perform L-shaped movement in a forward direction, the guide pipe drives the vial cap of the cryogenic vial to perform forward rotation and upward lifting movement, to unscrew the vial cap; and in a case that the cap screwing servo motor drives, via the rotation shaft, the protrusions to perform L-shaped movement in a reversed direction, the guide pipe drives the vial cap of the cryogenic vial to perform downward and reversed rotation movement, to screw the vial cap.

Preferably, the operation region is further provided with shakers in an integrated manner, and the shakers includes a Cell Factory shaker and a centrifuge bottle shaker; where the Cell Factory shaker includes an outer frame, a drive mechanism mounted on the outer frame, and a shaking platform configured to perform shaking under an action of the drive mechanism; the drive mechanism of the Cell Factory shaker includes a servo motor and an eccentric shaft connected to an output end of the servo motor, and the servo motor is provided with a return-to-zero device; the shaking platform is arranged at a top end of the eccentric shaft; a surface of the shaking platform is provided with a Cell Factory clamping component, a Cell Factory required to be shaken by the Cell Factory shaker are mounted at the Cell Factory clamping component through a Cell Factory support frame;

the centrifuge bottle shaker includes a shaking unit, and the shaking unit includes:

a drive mechanism for centrifuge bottle shaker, having an output shaft for outputting a rotating torque;

an eccentric shake disk arranged at an output end of the output shaft in an eccentric manner and configured to rotate around an axis of the output shaft; the eccentric manner is defined that an axis of the eccentric shake disk is arranged in parallel with and in a preset distance from the axis of the output shaft;

a centrifuge bottle clamp, where the centrifuge bottle clamp is arranged at the eccentric shake disk in a manner that the centrifuge bottle clamp has an elastic degree of freedom in an axial direction with respect to the eccentric shake disk; the axial direction is a direction in parallel with the axis of the output shaft.

Preferably, the Cell Factory support frame has a Cell Factory placing box; and where the Cell Factory placing box includes:

a bottom plate, a back plate, and two side plates, where the bottom plate is partially sunken inward, to form a Cell Factory limiting groove; and a Cell Factory locking structure, where the Cell Factory locking structure has a Cell Factory limiting element and a Cell Factory locking element, one end of the Cell Factory limiting element is mounted at an area of the back plate corresponding to the Cell Factory limiting groove in a manner that the Cell Factory limiting element has one rotational degree of freedom, and one end of the Cell Factory locking element is mounted at an area of the bottom plate corresponding to the Cell Factory limiting groove in a manner that the Cell Factory locking element has one rotational degree of freedom; another end of the Cell Factory limiting element and another end of the Cell Factory locking element are allowed to be locked with each other, after being locked, the Cell Factory limiting element is in parallel with the bottom plate, and the Cell Factory locking element is in parallel with the back plate; or the Cell Factory placing box includes:

a bottom plate, a back plate, and two side plates, where the bottom plate is partially sunken inward, to form a Cell Factory limiting groove; and a Cell Factory locking structure, where the Cell Factory locking structure has a Cell Factory limiting element and a Cell Factory locking element, one end of the Cell Factory limiting element is mounted at one of the two side plates in a manner that in a manner that the Cell Factory limiting element has one rotational degree of freedom, and one end of the Cell Factory locking element is mounted at the other one of the two side plates in a manner that the Cell Factory locking element has one rotational degree of freedom; another end of the Cell Factory limiting element and another end of the Cell Factory locking element are allowed to be locked with each other, after being locked, the Cell Factory limiting element is in parallel with the bottom plate.

Preferably, the number of the shaking unit is plural, the plurality of shaking units are uniformly arranged, the eccentric shake disk of each of the shaking units is mounted on a crankshaft via a bearing, and adjacent two eccentric shake disks are elastically connected with each other.

Preferably, the centrifuge bottle clamp has a bottom seat, a centrifuge bottle support seat and an elastic clamping element; where the centrifuge bottle support seat is integrated at the bottom seat, and an upper surface of the centrifuge bottle support seat is partially sunken inward to form a bottom positioning portion matching a bottom of the centrifuge bottle; and the elastic clamping element has a plurality of upright posts and at least one auxiliary ring, the plurality of upright posts each has one end fixed to the bottom seat, the plurality of upright posts are arranged to surround the centrifuge bottle support seat to form a centrifuge bottle side clamping structure, the plurality of upright posts each has another end bent backward to form a reinforcing ring; the auxiliary ring surrounds all the upright posts and is connected to lower portions of all the upright posts.

The beneficial effects are as follows.

From the above technical solutions, it can be seen that the technical solutions of the present invention provide a full-automatic cell production line, which is divided into a culture region and an operation region. The culture region is configured for the culture of cells, and the operation region is configured for completing the operations of liquid exchange, passaging and freezing and aliquoting of cells, etc.

The operations in the Cell Factory operation region realizes the operations of automatic liquid exchange, automatic digestion and collection, automatic glue spreading, etc. of the Cell Factory; at the same time, it realizes the operations of automatic liquid adding, automatic aliquoting, automatic centrifugation, automatic shaking, automatic sieving, automatic sampling and automatic aliquoting of the cell suspension, which truly realizes the automation and intelligence of the whole process of cell culture production.

Some liquid pipelines of the devices in the operation region are equipped with automatic sterilization device and washing device. Online SIP and CIP can be realized by program switching.

The automatic entry and exit of materials in cell production are performed through transfer window and operation table, to realize unmanned operation of the whole process of cell production.

In summary, automatic unmanned culture of cells is realized, intelligent software is used to achieve automatic culture management, and Cell Factory operation is automatically requested according to the progress of the cell production.

BRIEF DESCRIPTION OF THE DRAWINGS

In FIG. 1:

| 1 | culture region, | 2 | operation region. |

Figure 2:
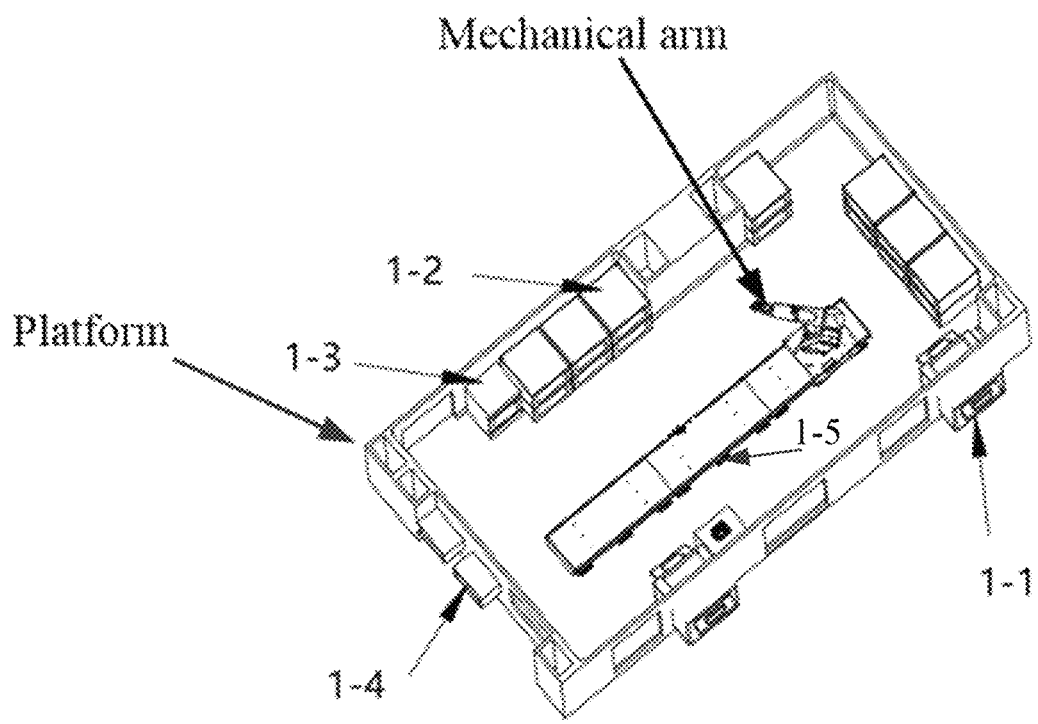
Figure 3:
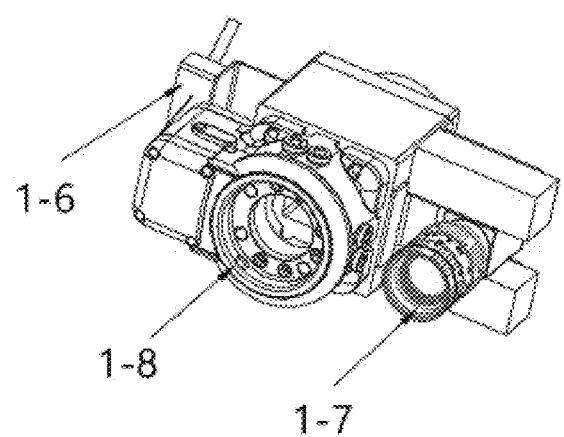

FIG. 2 is a schematic view showing the structure of a culture region according to the present invention;

FIG. 3 is a schematic view showing the structure of a gripper of a mechanical arm;

In FIGS. 2 and 3:

| 1-1 | automatic transfer window, | 1-2 | culture area, |
| 1-3 | refrigeration area, | 1-4 | transfer window, |
| 1-5 | track, | 1-6 | distance measuring sensor, |

| | | | |
|---|---|---|---|
| 1-7 | surveillance camera, | 1-8 | quick-change chuck, |
| 1-9 | mechanical arm. | | |

Figure 4:
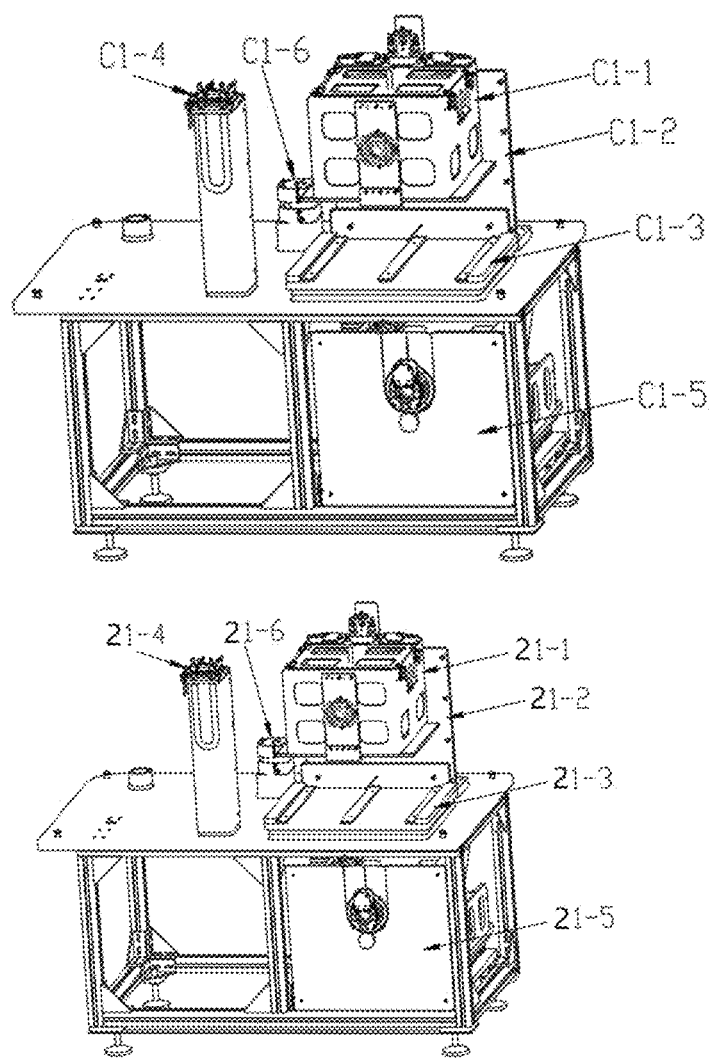
Figure 5:
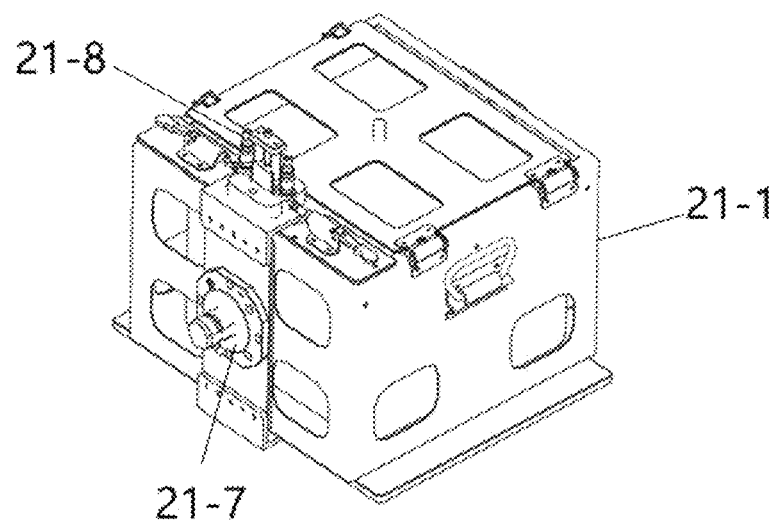
Figure 6:
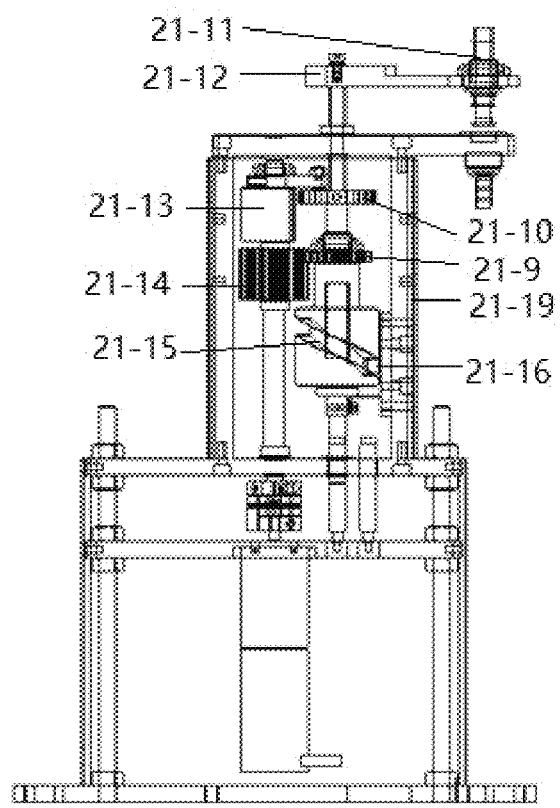
Figure 7:
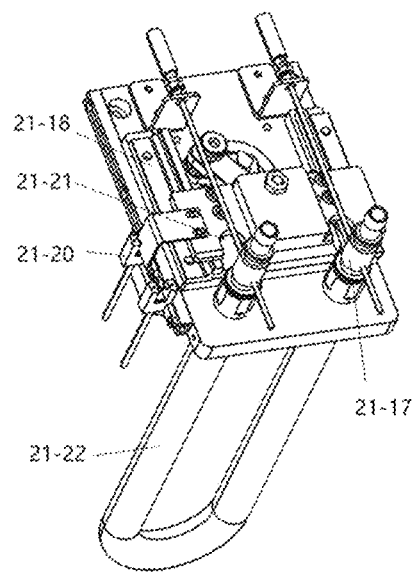

FIG. 4 is a schematic view showing the structure of a liquid storage table according to the present invention;

FIG. 5 is a schematic view showing the structure of a liquid storage box of the liquid storage table according to the present invention;

FIG. 6 is a schematic perspective view showing the structure of a pipeline switching device of the liquid storage table according to the present invention;

FIG. 7 is a schematic view showing the structure of a sterilization pipeline locking structure;

In FIGS. 4 to 7:

| | | | |
|---|---|---|---|
| 21-1 | liquid storage box, | 21-2 | liquid storage bag shaking device, |
| 21-3 | liquid storage bag weighing table, | 21-4 | pipeline switching device, |
| 21-5 | waste liquid collection device, | 21-6 | peristaltic pump, |
| 21-7 | fixing disk, | 21-8 | discharge pipeline, |
| 21-9 | gear disk, | 21-10 | follower disk, |
| 21-11 | pipe switching joint, | 21-12 | bracket, |
| 21-13 | drive motor, | 21-14 | gear shaft, |
| 21-15 | guide rod, | 21-16 | guide protrusion, |
| 21-17 | end of sterilization pipeline of liquid storage table, | | |
| 21-18 | slideway, | 21-19 | external support, |
| 21-20 | U-shaped optoelectronic switch, | 21-21 | locking slot, |
| 21-22 | sterilization pipeline of liquid storage table. | | |

Figure 8:
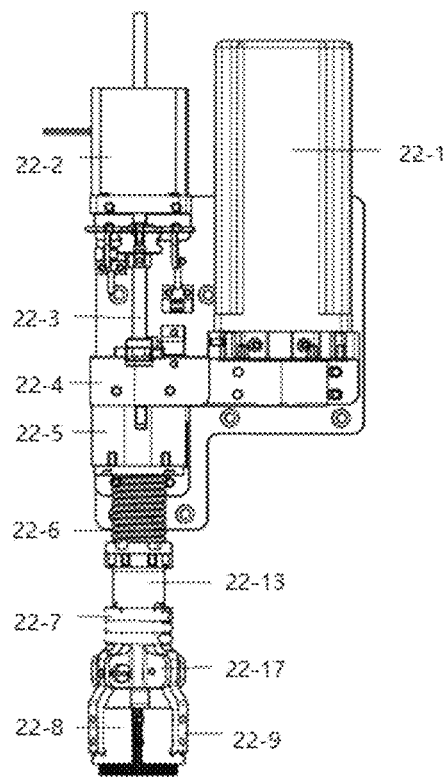
Figure 9:
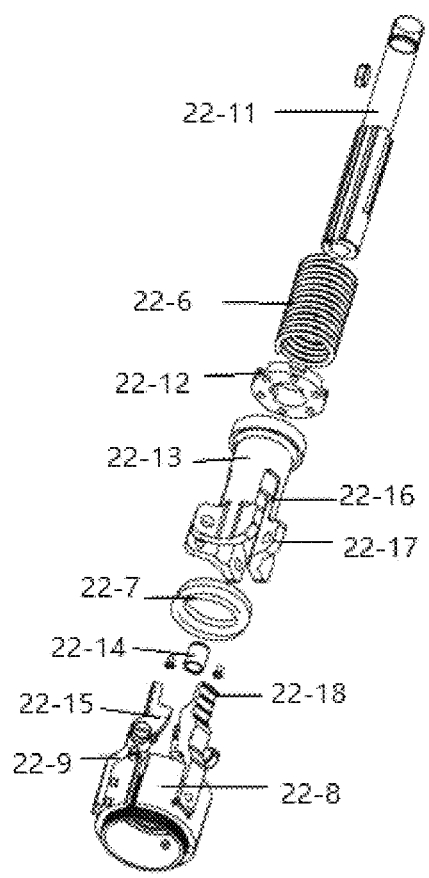
Figure 10:
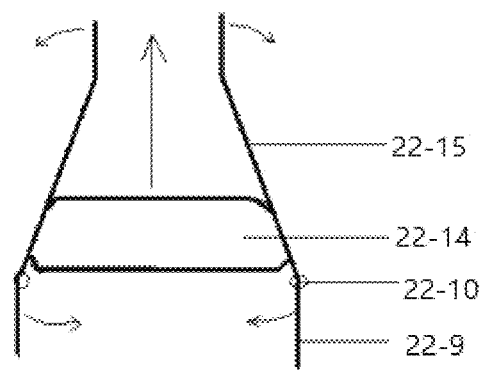
Figure 11:
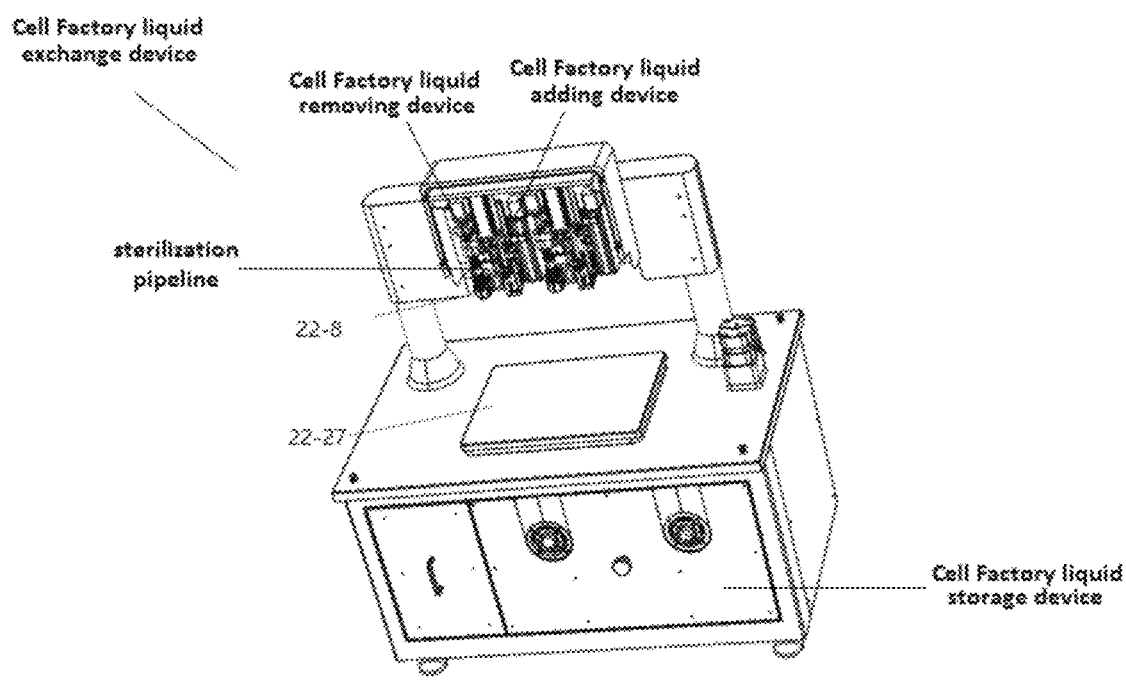
Figure 12:
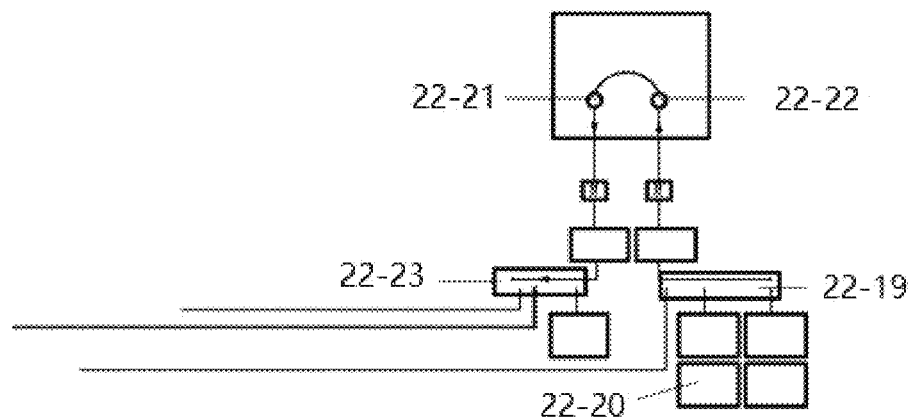
Figure 13:
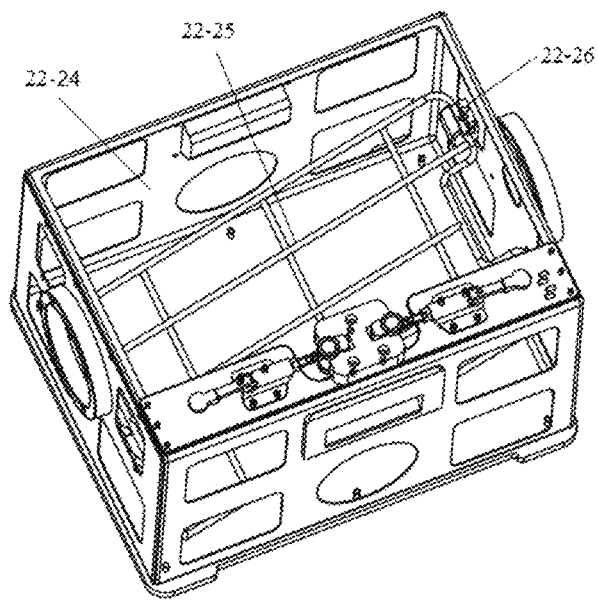

FIG. 8 is a front view of a cap twisting device according to the present invention;

FIG. 9 is an exploded structural view showing a part of the cap screwing device according to the present invention;

FIG. 10 is a view showing the action principle of a control terminal adjusting an opening degree of a clamping jaw assembly according to the present invention;

FIG. 11 is an overall schematic view showing a liquid exchange system of a Cell Factory according to the present invention;

FIG. 12 is a view showing pipeline connection in a sterilization process;

FIG. 13 is a schematic view showing the structure of a liquid storage device according to the present invention;

In FIGS. 8 to 13:

| | | | |
|---|---|---|---|
| 22-1 | cap twisting servo motor, | | |
| 22-2 | motor for opening and closing clamping jaw, | | |
| 22-3 | clamping jaw control shaft, | 22-4 | belt, |
| 22-5 | support plate, | 22-6 | buffer element, |
| 22-7 | elastic ring, | 22-8 | clamping plate, |
| 22-9 | clamping portion, | 22-10 | mounting pivot, |
| 22-11 | cap twisting main shaft, | 22-12 | positioning device, |
| 22-13 | shaft sleeve for mounting clamping jaw, | | |
| 22-14 | control terminal, | 22-15 | slope surface structure, |
| 22-16 | passage, | 22-17 | lug boss, |
| 22-18 | slot, | 22-19 | liquid adding peristaltic pump, |
| 22-20 | sterilization source, | 22-21 | liquid removing needle, |
| 22-22 | liquid adding needle, | 22-23 | liquid removing peristaltic pump, |
| 22-24 | liquid storage tank, | 22-25 | inclined surface, |
| 22-26 | liquid storage bag fixing portion, | 22-27 | weighing table. |

In the figures, arrows represent rotating directions.

Figure 14:
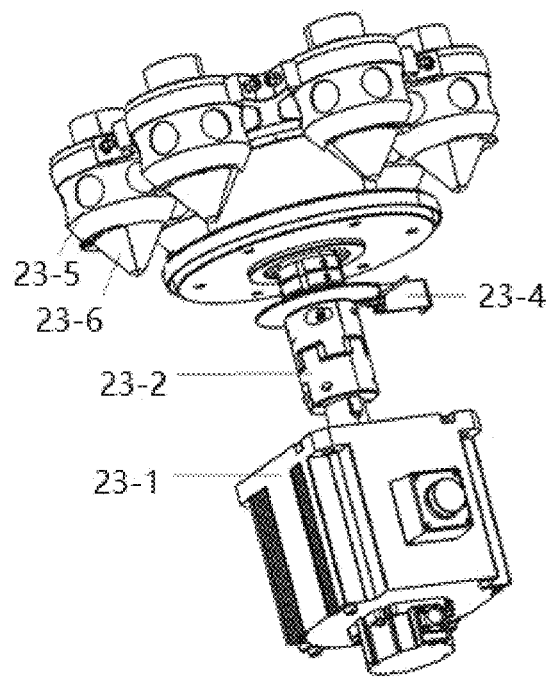
Figure 15:
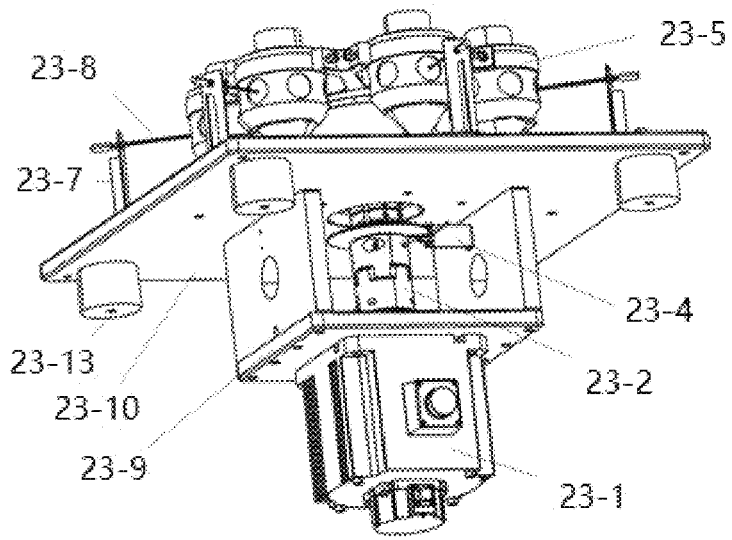
Figure 16:
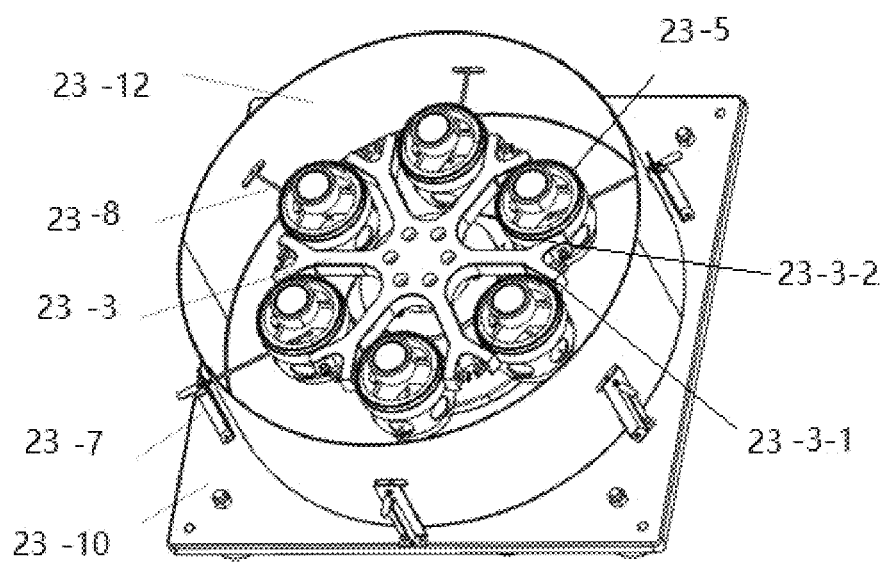
Figure 17:
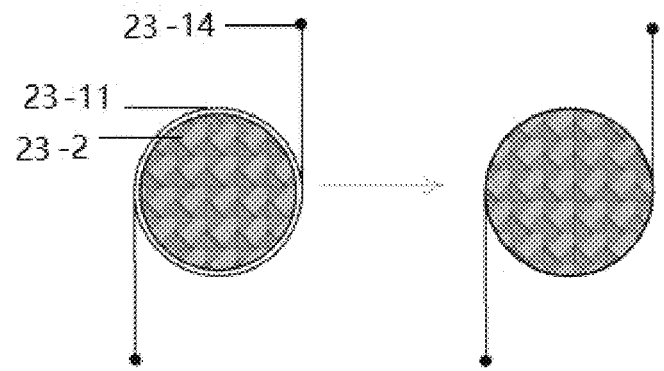

FIG. 14 is a schematic view showing the mounting structure of a drive mechanism of a centrifuge and a horizontal rotor according to the present invention from a first perspective view;

FIG. 15 is a schematic view showing the mounting structure of the drive mechanism of the centrifuge and the horizontal rotor according to the present invention from a second perspective view;

FIG. 16 is a schematic view showing the structure of the horizontal rotor according to the present invention;

FIG. 17 is a view showing the working principle of an emergency braking mechanism of the centrifuge;

In FIGS. 14 to 17:

| | | | |
|---|---|---|---|
| 23-1 | servo motor, | 23-2 | drive shaft, |
| 23-3 | horizontal rotor, | 23-3-1 | first arm of force component, |
| 23-3-2 | second arm of force component, | 23-4 | zero-position switch, |
| 23-5 | hanging basket, | 23-6 | centrifuge container, |
| 23-7 | optical fiber detection switch, | 23-8 | signal, |
| 23-9 | support, | 23-10 | buffer plate, |
| 23-11 | annular heated body, | 23-12 | annular inner cover, |
| 23-13 | buffer element, | 23-14 | flange. |

Figure 18:
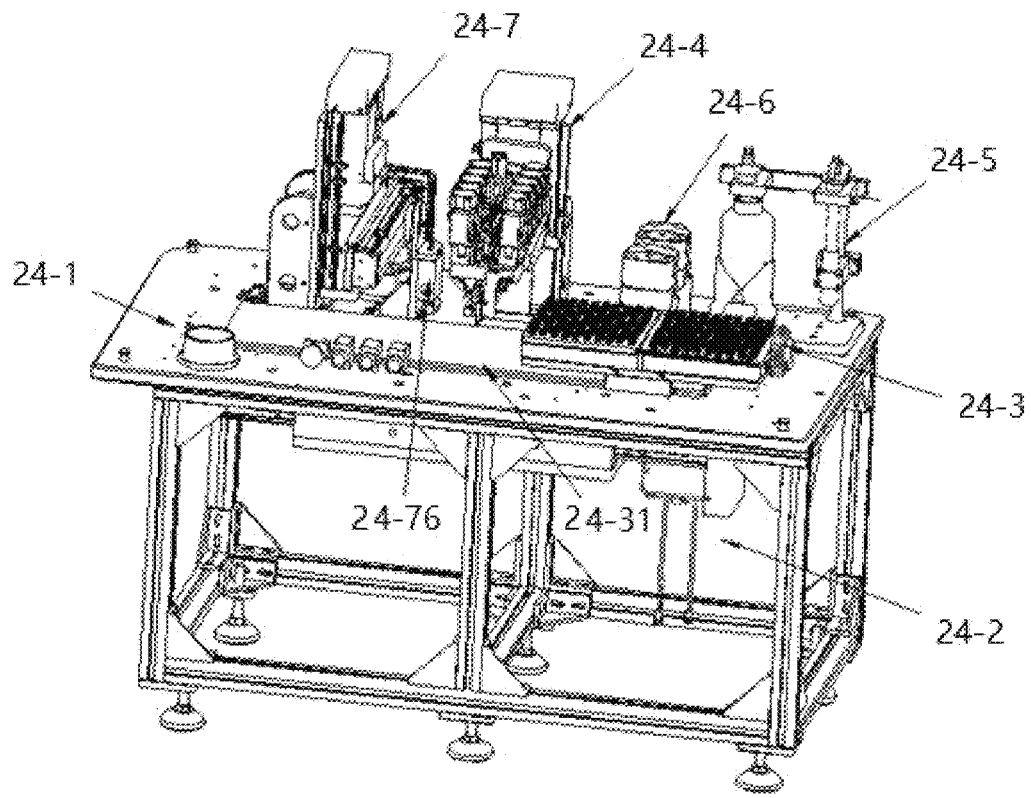
Figure 19:
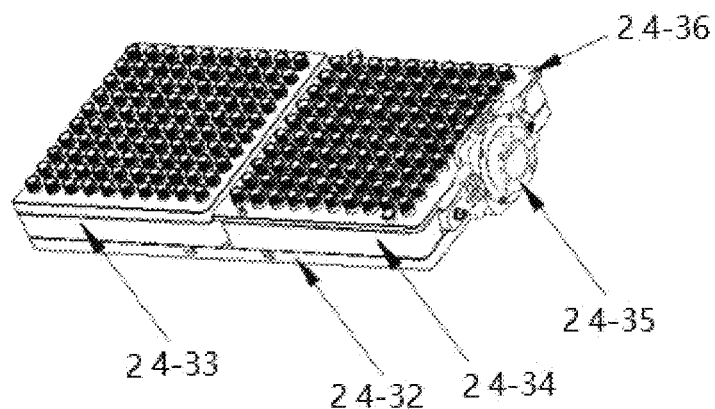
Figure 20:
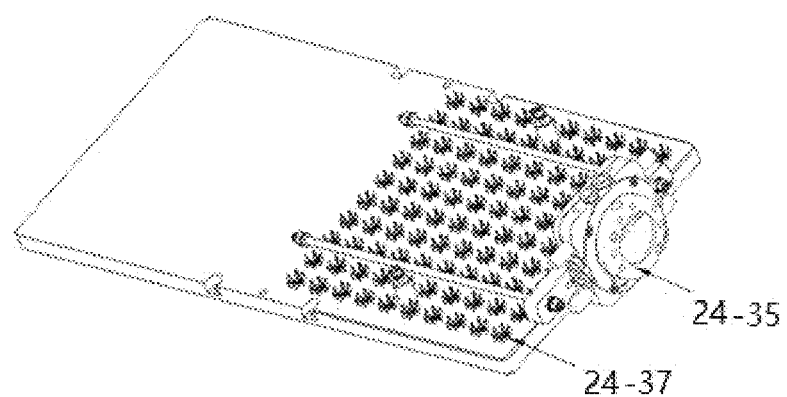
Figure 21:
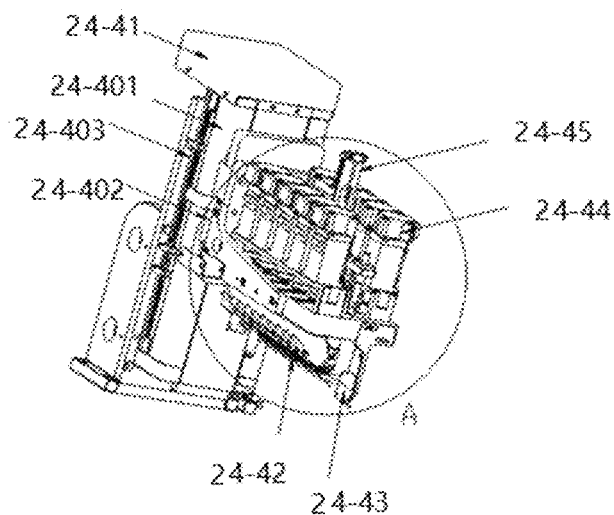
Figure 22:
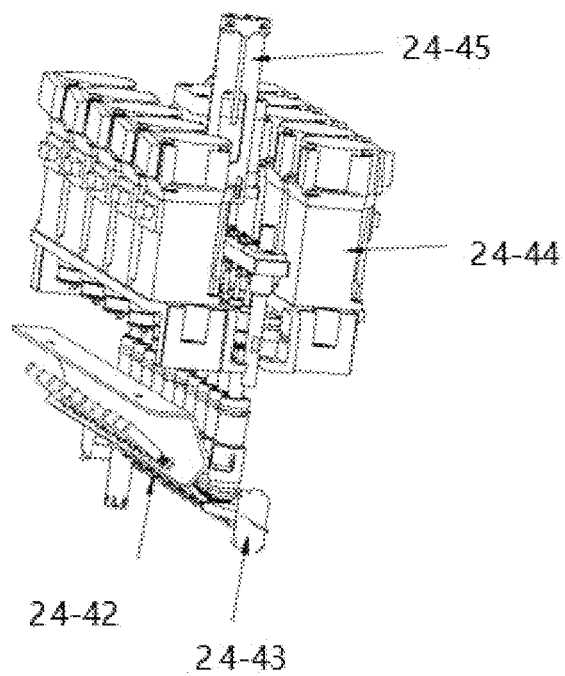
Figure 23:
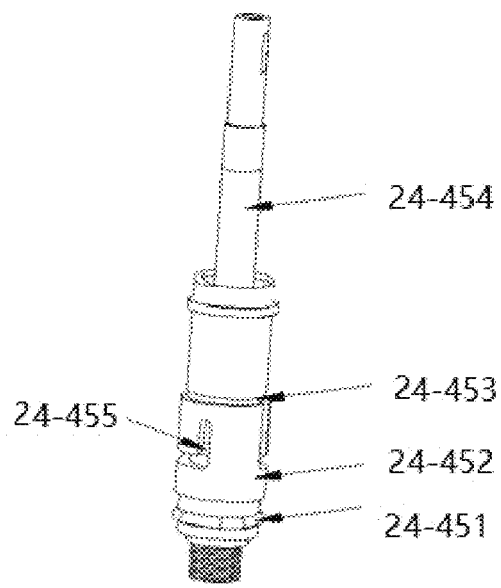
Figure 24:
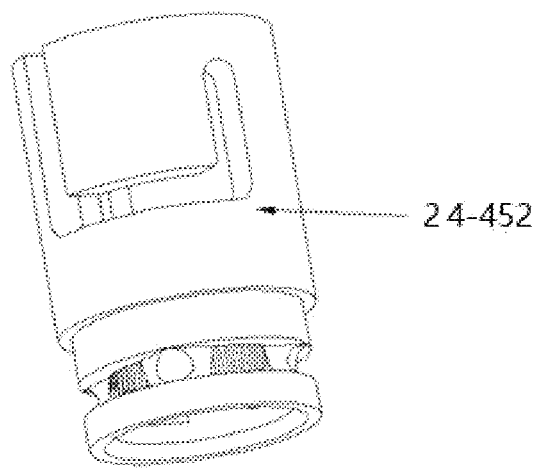
Figure 25:
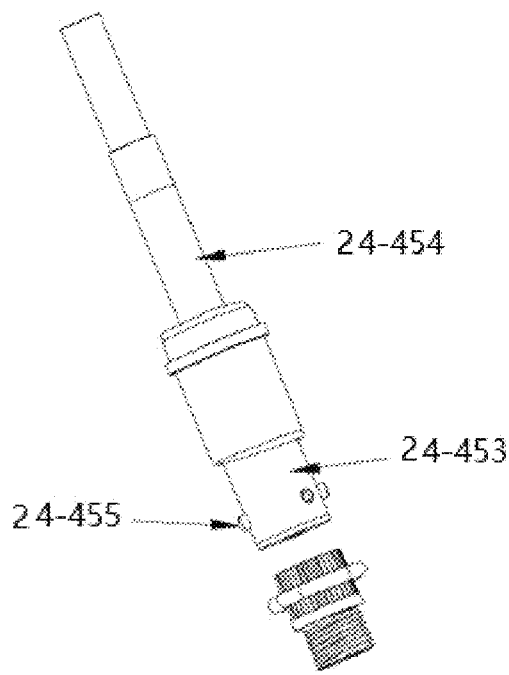
Figure 26:
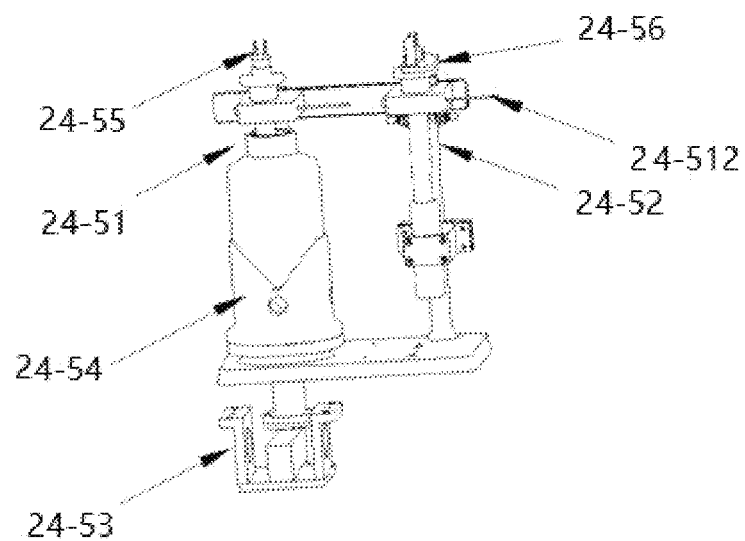
Figure 27:
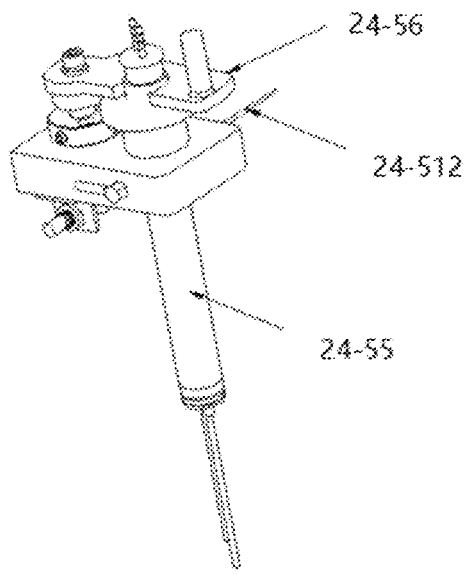
Figure 28:
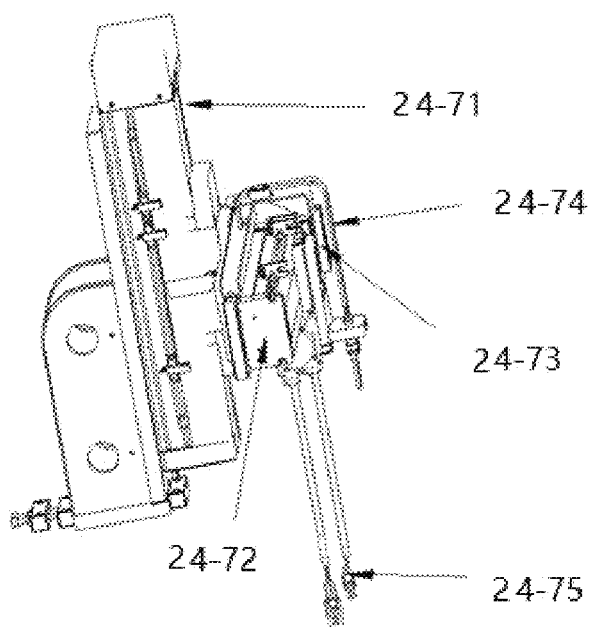
Figure 29:
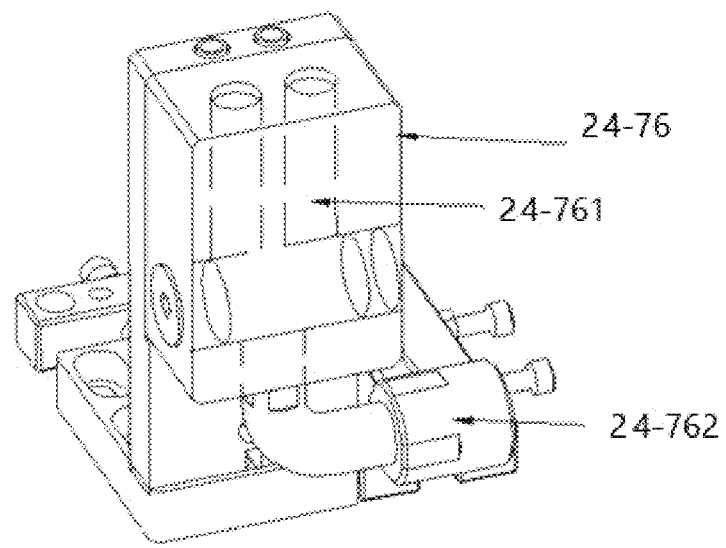

FIG. 18 is a schematic view showing the structure of an automatic cryogenic vial opening and aliquoting device;

FIG. 19 is a schematic view showing the structure of a translation module;

FIG. 20 is a schematic view showing the structure of a bottom of the translation module;

FIG. 21 is a schematic view showing the structure of a cap screwing main shaft;

FIG. 22 is a schematic view showing the structure of a portion of the cap screwing main shaft;

FIG. 23 is a schematic view showing the structure of a cap detaching device;

FIG. 24 is a schematic view showing the structure of a guide pipe;

FIG. 25 is a schematic view showing the structure of a slider moving pipe;

FIG. 26 is a schematic view showing the structure of a liquid adding device;

FIG. 27 is a schematic view showing the structure of a liquid removing double-needle of the liquid adding device;

FIG. 28 is a schematic view showing the structure of a liquid adding main shaft;

FIG. 29 is a schematic view showing the structure of a sterilization switching device;

In FIGS. 18 to 29:

| | | | |
|---|---|---|---|
| 24-1 | support platform, | 24-2 | electric control cabinet, |
| 24-3 | translation module, | 24-31 | base plate slideway, |
| 24-32 | pallet slider, | 24-33 | first tray pallet, |
| 24-34 | second tray pallet, | 24-35 | robot gripper, |
| 24-36 | base plate, | 24-37 | cryogenic vial fixing shaft, |
| 24-4 | cap screwing main shaft, | 24-41 | lifting module for cap screwing, |

| | | | |
|---|---|---|---|
| 24-401 | guide rail, | 24-402 | slider, |
| 24-40 | motor, | 24-42 | vial cap detection device, |
| 24-43 | vial body detection device, | 24-44 | cap screwing servo motor, |
| 24-45 | vial cap detaching device, | 24-451 | spring, |
| 24-452 | guide pipe, | 24-453 | slider moving pipe, |
| 24-454 | casing pipe mounting plate, | 24-455 | protrusion, |
| 24-5 | liquid adding device, | 24-51 | liquid adding platform, |
| 24-512 | laser sensor, | 24-52 | sterilization platform, |
| 24-53 | centrifuge bottle weighing platform, | 24-54 | centrifuge bottle placing table, |
| 24-55 | liquid removing double-needle, | 24-56 | pushrod locking device, |
| 24-6 | liquid removing peristaltic pump, | 24-7 | liquid adding main shaft, |
| 24-71 | lifting module for liquid adding, | | |
| 24-72 | translation module for liquid adding, | | |
| 24-73 | basic plate, | 24-74 | liquid adding needle, |
| 24-75 | cable joint, | 24-76 | sterilization switching device, |
| 24-761 | butting pipe, | 24-762 | outlet pipe. |

Figure 30:
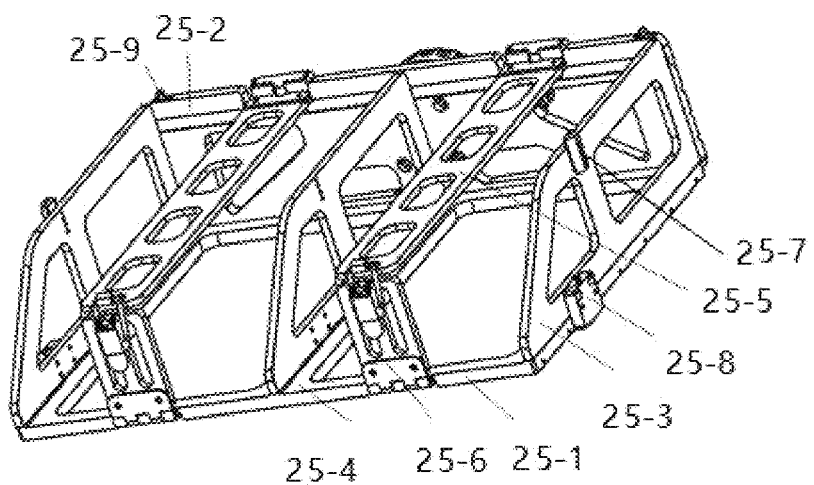
Figure 31:
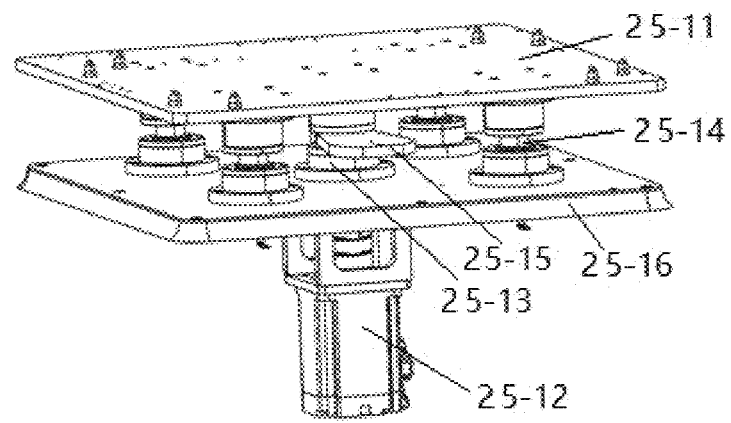

FIG. 30 shows a Cell Factory support frame according to the present invention;

FIG. 31 is a schematic view showing the inner structure of a Cell Factory shaker according to the present invention;

In FIGS. 30 and 31:

| | | | |
|---|---|---|---|
| 25-1 | bottom plate, | 25-2 | back plate, |
| 25-3 | side plate, | 25-4 | Cell Factory limiting groove, |
| 25-5 | Cell Factory limiting element, | 25-6 | Cell Factory locking element, |
| 25-7 | first locking element, | 25-8 | second locking element, |
| 25-9 | positioning element, | 25-11 | shaking platform mounting area, |
| 25-12 | servo motor, | 25-13 | eccentric shaft, |
| 25-14 | synchronous eccentric shaft, | 25-15 | balancing plate, |
| 25-16 | auxiliary mounting plate. | | |

Figure 32:
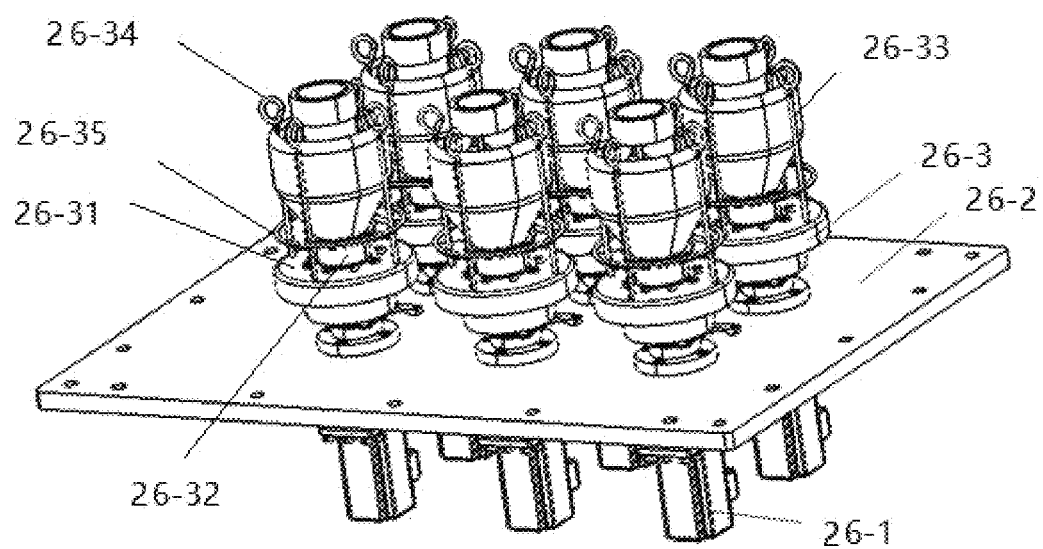

FIG. 32 is a schematic view showing the arrangement of a plurality of shaking units of a centrifuge bottle shaker according to the present invention;

In FIG. 32:

| | | | |
|---|---|---|---|
| 26-1 | drive mechanism, | 26-2 | shaker base plate, |
| 26-3 | centrifuge bottle clamp, | 26-31 | bottom seat, |
| 26-32 | centrifuge bottle support seat, | 26-33 | elastic clamping element, |
| 26-34 | reinforcing ring, | 26-35 | auxiliary ring. |

DETAILED DESCRIPTION OF THE EMBODIMENTS

Figure 1:
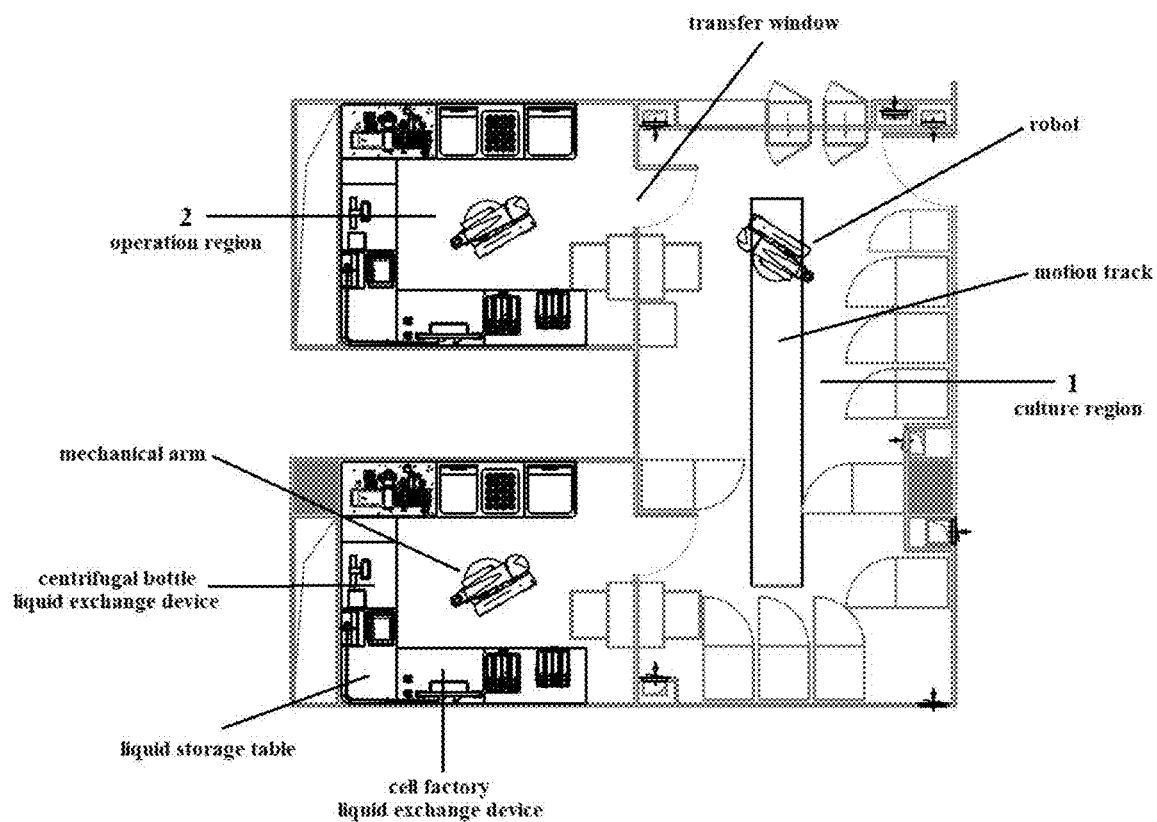
FIG. 1 is a schematic view showing the structure of a full-automatic cell production line according to the present invention.

In conjunction with FIG. 1, a full-automatic cell production line is provided, including a culture region 1 (with a B-level environment at the lowest for cost saving) and an operation region (with an A-level environment for biosafety). The culture region 1 is used for cell culture and refrigeration; the operation region 2 is used for operations in a cell culture process, such as liquid exchange, centrifugation and freezing. According to the present invention, a mechanical arm is employed for operation in the culture region 1 and the operation region 2 respectively, to achieve full automation of cell culture.

To better illustrate the technical solutions of the present invention, description will be made hereinafter in conjunction with specific embodiments.

FIGS. 2 and 3 Regarding the Culture Region

As shown in FIG. 2, the culture region includes a B-level platform body, where the B-level platform body includes a culture area 1-2, a refrigeration area 1-3 and a sterile robot equipped with a motion track 1-5. Preferably, a transfer window 1-4 is further provided.

The culture area, the refrigeration area 1-3 and the transfer window 1-4 are arranged to surround the motion track 1-5 and are all located within an operation area of the robot; the motion track 1-5 of the robot is arranged at a bottom of the B-level platform body in a linear manner. The motion track 1-5 of the robot is made of stainless steel. The motion track 1-5 is positioned in a manner that a gripper of the robot can reach any working area of the B-level platform body. The culture area 1-2 is equipped with a plurality of incubators, the incubators are each provided with an inner door and an outer door, the outer door is provided with a display screen, and the inner door and the outer door are each provided with a handle, for opening and closing by a chuck of the robot. The refrigeration area 1-3 is equipped with a plurality of refrigerators, the refrigerators are set at 4° C. as thermostatic freezers. The incubators and the refrigerators are powered and controlled individually. Besides, the incubator is provided with a temperature data monitoring system for real-time data monitoring.

With reference to FIG. 3, the transfer window 1-4 is arranged to have as at least one window, and the B-level platform body transfers materials with the outside through the transfer window 1-4. The operation region transfers materials with the culture region through the automatic transfer window 1-1. As shown in FIG. 2, a distance measuring sensor 1-6, a surveillance camera 1-7, and a quick-change chuck 1-8 are arranged at the gripper of the robot. The distance measuring sensor 1-6 and the surveillance camera 1-7 cooperate with each other to achieve position detection, transmission of the situation of the materials and areas in the B-level platform body to the monitoring system, and real-time monitoring respectively. The quick-change chuck 1-8 is configured to realize various operations of the robot.

In summary, the B-level platform body cooperates with motions of automatic transfer window 1-1, to achieve full-automatic unmanned operation of cell culture, the automatic monitoring and management functions of cell culture is realized, operations such as fluid change in a later period can be requested automatically according to the situation of cell culture.

FIGS. 4 to 32 Regarding the Operation Region

As shown in FIGS. 4 to 7, the operation region is provided with a liquid storage table, a Cell Factory liquid exchange device and a centrifugal bottle liquid exchange device in an integrated manner; the liquid storage table, the Cell Factory liquid exchange device and the centrifugal bottle liquid exchange device are arranged around the mechanical arm in the operation region and are located within a control range of the mechanical arm. A centrifuge bottle shaker, a Cell Factory shaker, a cryogenic vial opening and aliquoting device, full-automatic centrifuge, etc. are also integrated in the operation region. The liquid storage table, the Cell Factory liquid exchange device, the centrifugal bottle liquid exchange device, the centrifuge bottle shaker, the Cell Factory shaker, the cryogenic vial opening and aliquoting device, and the full-automatic centrifuge integrated in the operation region are arranged to surround the mechanical arm located in the operation region. Operation of the mechanical arm to each of the devices has a zero position, and the operation of the mechanical arm to each device by is performed when the device is in at zero position, and each device is equipped with an automatic cap opening device and a zero position detection device.

Materials are transferred between the culture region and the operation region through a transfer window, the transfer window has a transfer turnplate and a transfer turnplate drive mechanism; the transfer turnplate has a zero position for the robot of the culture region to pick up and place the materials, and a working position for the mechanical arm of the operation region to pick up and place the materials; the transfer turnplate is configured to be driven by the transfer turnplate drive mechanism to rotate, to achieve switching between the zero position and the working position.

The operation region is specifically as follows. As shown in FIG. 4, the liquid storage table includes a liquid storage bag swaying mechanism, a waste liquid collection device 21-5, a pipeline switching device 21-4, a sterilization pipeline table and a liquid storage bag weighing table 21-3.

The liquid storage bag swaying mechanism includes a liquid storage box 21-1 and a liquid storage bag shaking device 21-2. As shown in FIG. 5, the liquid storage box 21-1 is set as a frame body, a mechanical snap structure is used for fixation, to open or close the liquid storage box 21-1. An inside of the liquid storage box 21-1 is used for placing the liquid storage bag; an upper end of the liquid storage box 21-1 is provided with a liquid collection pipe; front and rear ends of the liquid storage box 21-1 are provided with a fixing disk 21-7 and a robot gripper disk, respectively, and the liquid storage box 21-1 is automatically placed on the liquid storage bag shaking device 21-2 by the robot, to be fixed with the liquid storage bag shaking device 21-2. The liquid collection pipe at the upper end of the liquid storage box 21-1 is in communication with the liquid storage box 21-1 in a run-through manner, thus liquid adding can be realized.

The shaker drive mechanism and the storage bag box are drivably connected in a detachable manner. In some embodiments, the liquid storage box 21-1 and the liquid storage bag shaking device 21-2 are fixed as follows. The fixing disk 21-7 at the side of the liquid storage box 21-1 includes a circular bottom disk and a protruding block; the liquid storage bag shaking device 21-2 includes a fixing platform, a clamping disk, a decelerator and a motor, and the fixing platform is provided with a through hole; one side of the clamping disk is connected to the decelerator, and the other side of the clamping disk passes through the through hole to be fixedly connected to the fixing disk 21-7. Specifically, The protruding block of the fixing disk 21-7 passes through a hollow position at a middle of the clamping disk, to make a surface of the circular bottom disk and a surface of the clamping disk be fitted to each other, so as to realize fixation. The liquid storage bag shaking device 21-2 is driven by a 40-watt motor and the decelerator with a reduction ratio of 30, to achieve uniformity of operation. This swaying can realize the sway of the liquid storage bag at any angle and frequency, to achieve the function of mixing the liquid in the liquid storage bag. The fixing platform is equipped with a limiting laser detection sensor, which is used to detect the presence or absence of the device in the liquid storage box 21-1.

A waste liquid collection device 21-5 is provided with a waste liquid collection box. A discharge pipeline 21-8 is arranged at the waste liquid collection box, the discharge pipeline 21-8 is in communication with a Cell Factory liquid removing device or a centrifuge bottle liquid removing device through a peristaltic pump 21-6, to collect the waste liquid into the waste liquid collection box. The waste liquid collection box employs a drawer-type structure, a robot handle is arranged at a side end of the waste liquid collection box, and extension and retraction of the drawer is realized by the robot; the drawer is further provided with an extension and retraction limiting switch and a mechanical seizing device, to facilitate detection of whether the drawer is fully opened or closed.

Since the whole production line is controlled by automation, the pipeline switching between the washing passage and the sterilization passage needs to be controlled by automation, so a side where the waste liquid collection box is located is equipped with the pipeline switching device 21-4. As shown in FIG. 6, the pipeline switching device 21-4 includes an external support 21-19, and a switching device drive mechanism and a reversing mechanism both supported by the external support 21-19. The external support 21-19 is provided with a guide protrusion, and a sterilization pipeline is also arranged on the external support 21-19; the sterilization pipeline on the external support 21-19 has one end in communication with a liquid removing pipe of the Cell Factory liquid exchange device through a pipe switching joint 21-11, and the other end in communication with a sterilization pipeline of liquid storage table 21-22. The switching device drive mechanism includes a drive motor 21-13 provided with a protruding element in a fixed manner, rotation output of the drive motor 21-13 is performed by a gear shaft 21-14. The reversing mechanism has a driven shaft, a pipe switching joint 21-11 is fixed at a beginning end of the driven shaft through a bracket 21-12, and the bracket 21-12 is allowed to rotate with respect to the driven shaft under an action of an external force (relative rotation between the bracket 12-21 and the driven shaft may be realized by a shaft sleeve, or by any technical solution in the conventional technology which can realize the technology, only the implementation of this technology is involved in this application). The pipe switching joint 21-11 has a working position for inserting into the sterilization pipeline on the external support 21-19 during the rotation of the bracket 21-12. A follower disk 21-10, a gear disk 21-9 and a guide rod 21-15 are sequentially arranged at a shaft body section of the driven shaft; the follower disk 21-10 is connected to the drive motor 21-13; the follower disk 21-10 is located below the protruding element; the gear disk 21-9 and the gear shaft 21-14 are in gear transmission; an outer surface the guide rod 21-15 is provided with a helical groove configured for the guide protrusion 21-16 to slide in; a beginning end of the helical groove has a beginning horizontal segment, and a tail end of the helical groove has a tail horizontal segment.

The operation principle is that: the drive motor 21-13 rotates, the gear shaft 21-14 drives the gear disk 21-9 to rotate, and the gear disk 21-9 drives the driven shaft to rotate. When the guide protrusion 21-16 is located at a beginning end of the helical groove (the beginning end is defined as the end located near the end of the pipe switching joint 21-11 fixed at the driven shaft, and the other end is defined as a tail end), at the start of the rotation of the drive motor 21-13, the pipe switching joint 21-11 is located at a zero position, at this time, it is convenient for the mechanical arm to connect the liquid removing pipe of the Cell Factory liquid exchange device to the pipe switching joint 21-11. The guide protrusion 21-16 slides horizontally along a circle in the beginning horizontal segment, at this time, the driven shaft drives the pipe switching joint 21-11 to rotate to be adjusted to a switched working position (to connect with the sterilization pipeline on the external support 21-19); at the same time, the follower disk 21-10 only performs rotation around the axis. By the time the guide protrusion 21-16 passes the beginning horizontal segment and reaches a helical segment, the pipe switching joint 21-11 also reaches the corresponding working position. With the rotation of the drive motor 21-13, the guide protrusion 21-16 rotates downward around the helical groove, while the follower disk 21-10 drives the drive motor 21-13 and the gear shaft 21-14 to move downward synchronously so that the gear disk 21-9 and the gear shaft 21-14 always rotate synchronously, and the pipe switching joint is locked by the corresponding working position and only extends downward relative to the working position, in this case, the bracket 21-12 will rotate relative to the driven shaft. When the guide protrusion 21-16 rotates to the tail horizontal segment, the pipe switching joint 21-11 reaches a fixed working position; the guide protrusion 21-16 rotates in the horizontal segment, and the working position is fixed by the tail horizontal segment when the pipe switching joint 21-11 is working, so as to avoid the pipe switching joint from falling off when it is working.

The sterilization pipeline table is provided with a sterilization pipeline locking structure. Referring to FIG. 7, the sterilization pipeline locking structure includes a sterilization pipeline of liquid storage table 21-22, stepper motor and a rocker-slider structure.

One end 21-17 of the sterilization pipeline of liquid storage table 21-22 is connected to the pipe switching joint 21-11, and the other end of the sterilization pipeline of liquid storage table is in communication with an external sterilization condensing pipeline when being used for sterilization for the Cell Factory liquid exchange device, and in communication with a liquid adding pipe of the centrifuge bottle liquid exchange device when being used for combined sterilization for the Cell Factory liquid exchange device and the centrifuge bottle liquid exchange device.

The rocker-slider structure includes a slider, a slideway 21-18 and a two-bar linkage. The slider has a locking slot 21-21, and the locking slot 21-21 is used to lock the sterilization pipeline of liquid storage table 21-22. The sterilization pipeline of liquid storage table 21-22 is provided with a sterilization pipeline joint of the sterilization pipeline of liquid storage table 21-22, an outer surface of the sterilization pipeline joint has varying diameters from top to bottom and has a smallest diameter at the uppermost, that is, the outer surface of the sterilization pipeline joint has a stepped structure. The locking slot 21-21 is defined as a groove matching the stepped structure, and the groove is engaged with the stepped structure by clamping. The locking slot 21-21 may be set to have a groove on a lower surface of the end, and the joint of the sterilization pipeline of liquid storage table 21-22 has a protrusion at a set position, the protrusion and the groove can cooperate to realize locking of the sterilization pipeline of liquid storage table 21-22 under high-temperature sterilization, mainly to avoid pipe vibration caused by high temperature and high pressure during the high-temperature sterilization. The slideway 21-18 is used to allow the slider to slide along a set route. One end of the two-bar linkage is driven by the stepper motor, and the other end is driven by the stepper motor to drive the slider to slide along the slideway 21-18. Herein, the sterilization pipeline switching is realized by employing the robot to insert the pipeline of the Cell Factory liquid removing device or the pipeline of the centrifuge bottle liquid removing device into the sterilization pipeline joint. Preferably, said sterilization pipeline locking structure is further provided with a pushing piece and two U-shaped optoelectronic switches 21-20, and the pushing piece has a zero position and detection position relative to the two U-shaped optoelectronic switches 21-20. The two U-shaped optoelectronic switches 21-20 are arranged at a side of the slideway 21-18 and pushing piece is provided at a side of the slider. When the slider is at the zero position, the locking slot 21-21 is away from the sterilization pipeline joint; and when the slider is at the detection position, the locking slot 21-21 locks the sterilization pipeline joint in a snap-in manner. The U-shaped optoelectronic switches 21-20 transmit linear photoelectric signals at the zero position and the detection position respectively.

The liquid storage bag weighing device is arranged above the waste liquid collection device 21-5 to save space, which includes a weight sensor, and a weighing platform that is detected by the weight sensor. The liquid storage bag weighing table 21-3 is used to weigh the weight of the liquid storage bag and the liquid therein in the liquid storage box. The robot can automatically place the liquid storage box 21-1 onto the liquid storage bag weighing table 21-3 through the robot gripper disk at a front end of the liquid storage box 21-1, and when the overall weight is measured and then the tare is removed, the weight of the liquid in the liquid storage bag can be known and the liquid aliquoting effect can be checked.

FIGS. 8 to 13 Showing the Schematic View of the Liquid Exchange Device of the Present Invention The Cell Factory liquid exchange device and the centrifuge bottle liquid exchange device have the substantially same structure, so they are described in a unified manner. The main idea is to use an automatic cap twisting device, an automatic liquid removing device (Cell Factory liquid removing device or centrifuge bottle liquid removing device), and an automatic liquid adding device (Cell Factory liquid storage device or centrifuge bottle liquid storage device), to control the cap twisting device to twist the cap, control the liquid removing device to suck liquid from a cell storage container, and control the liquid adding device to add the culture medium to the cell storage container by the control system (externally arranged), and finally the cap twisting device is used to twist the cap to seal the cell storage container, to finally realize the liquid adding or liquid removing of the cell storage container. A weighing platform is further provided, the weighing platform is located below the liquid adding device and the liquid removing device. When being used for Cell Factory liquid exchange, the Cell Factory liquid exchange device is provided with the Cell Factory liquid storage device, the Cell Factory removing device, the Cell Factory liquid adding device and the sterilization pipeline of the Cell Factory liquid exchange device in an integrated manner. When being used for centrifuge bottle liquid exchange, the centrifugal bottle liquid exchange device is provided with the centrifuge bottle liquid storage device, the centrifuge bottle liquid removing device, the centrifuge bottle liquid adding device, and the sterilization pipeline of the centrifuge bottle liquid exchange device in an integrated manners.

With reference to FIG. 13, the cap twisting device is used for unscrew or screw the cap of the cell storage container. The cap twisting device includes a cap twisting mechanism and a clamping jaw control mechanism.

The cap twisting mechanism includes a cap twisting main shaft 22-11 and a clamping jaw set. The cap twisting main shaft 22-11 is driven by the cap twisting servo motor 22-1 to rotate around its own axis, where a belt 22-4 may be used for driving. The clamping jaw set controlled by a motor for opening and closing clamping jaw 22-2 is mounted at an end of the cap twisting main shaft 22-11. The clamping jaw set includes a clamping jaw limiting component and a plurality of clamping jaws. The clamping jaw limiting component includes a plurality of elastic rings 22-7. Each of the clamping jaws includes a clamping portion 22-9, a mounting pivot 22-10 connected to the cap twisting main shaft 22-11 and a limiting structure arranged in sequence. The limiting structure corresponds to the cap twisting main shaft, one side of the limiting structure facing the cap twisting main shaft 22-11 has a slope surface structure 22-15, and the slope surface structure 22-15 is defined as a inclined surface structure inclined toward the cap twisting main shaft 22-11. The slope surface structures 22-15 of the clamping jaws of the clamping jaw set together form a cavity approximate to a circular truncated cone. Each of the plurality of elastic rings 22-7 is sleeved on another side of the limiting structure of each clamping jaw of the clamping jaw set.

In order to realize the adjustment of the opening degree of the clamping jaw set, the clamping jaw set has the following characteristics according to this application.

When the slope surface structures 22-15 of the clamping jaw set are arranged inside the cap twisting main shaft 22-11, each clamping jaw of the clamping jaw set has a mounting pivot 22-10 through which the clamping jaw is mounted on the cap twisting main shaft 22-11; each clamping jaw has a clamping portion 22-9, the clamping portion 22-9 being located at an end of the cap twisting main shaft 22-11; each jaw has a slope surface structure 22-15, which is located inside the end of the cap twisting main shaft 22-11. Besides, all the slope surface structures 22-15 of the clamping jaw set form the structure approximate to the circular truncated cone. An outside of each of the slope surface structures 22-15 is provided with slots 22-18, the elastic rings 22-7 are arranged outside the clamping jaw set, and each of elastic rings 22-7 is sleeved in the corresponding slots 22-18 located at outer sides of the clamping jaws of the clamping jaw set. When the control terminal 22-14 moves upward along an axis of a clamping jaw control shaft 22-3, the control terminal 22-14 overcomes the force of the elastic rings 22-7, making the cavity approximate to circular truncated cone of the clamping jaw set gradually change to a cylindrical cavity, at the same time, each clamping jaw rotates with the help of the mounting pivot 22-10, making a clamping size of the clamping jaw set become smaller. This structure is suitable for situations that the entire cap twisting main shaft 22-11 is raised by a height same as a rotate-out distance during the cap twisting process, or is lowered by a height same as a rotate-in distance during the cap twisting process (which is suitable for situations that the cap twisting main shaft 22-11 passes through the support plate 22-5 by means of threads and threaded hole). It is also suitable for situations that the mechanical arm gripping the Cell Factory is lowered by a height same as a rotate-out distance during the cap twisting process, or is raised by a height same as a rotate-in distance during the cap twisting process.

Preferably, the liquid exchange device is further provided with a buffer device. The buffer device includes a shaft sleeve for mounting clamping jaw 22-13 mounted on the cap twisting main shaft 22-11. The shaft sleeve for mounting clamping jaw 22-13 is capable of rotating coaxially with cap twisting main shaft 22-11, i.e. shaft sleeve for mounting clamping jaw 22-13 is fixed relative to the cap twisting main shaft 22-11 in a radial direction in a slide groove and slide boss connection manner; and, a length of the slide groove is longer than that of the slide boss. In another illustration way, if the shaft sleeve for mounting clamping jaw 22-13 is provided with a slide groove and cap twisting main shaft 22-11 is provided with a slide boss, and a length of the slide groove is longer than that of the slide boss, to ensure that the shaft sleeve for mounting clamping jaw 22-13 has a certain space for axial movement relative to the cap twisting main shaft 22-11; alternatively, if the shaft sleeve for mounting clamping jaw 22-13 is provided with a slide boss and the cap twisting main shaft 22-11 is provided with a slide groove, and a length of the slide groove is longer than that of the slide boss, to ensure that the shaft sleeve for mounting clamping jaw 22-13 has a certain space for axial movement relative to the cap twisting main shaft 22-11.

The clamping jaw set is mounted on the shaft sleeve for mounting clamping jaw 22-13 in such a way that it can rotate around a radial direction of the shaft sleeve for mounting clamping jaw 22-13. An end of the shaft sleeve for mounting clamping jaw 22-13 is provided with a passage 22-16 for rotation of the clamping jaw set. Specifically, each clamping jaw in the clamping jaw set has the mounting pivot 22-10 through which the clamping jaw is mounted on one end of the shaft sleeve for mounting clamping jaw 22-13. Preferably, the end of the shaft sleeve for mounting clamping jaw 22-13 has a plurality of lug bosses 22-17 protruding outward, a mounting bracket is formed between each two adjacent lug bosses 22-17, and the mounting pivot 22-10 is mounted on the mounting bracket through pins or screws. During rotation of the clamping jaw, a rotation path of the limiting structure of the clamping jaw passes through the passage 22-16.

Each clamping jaw has a clamping portion 22-9, and the clamping portion 22-9 is located outside the shaft sleeve for mounting clamping jaw 22-13. Each clamping jaw has a slope surface structure 22-15, and the slope surface structure 22-15 corresponds to the cap twisting main shaft 22-11. Besides, all the slope surface structures 22-15 of the clamping jaw set form the circular truncated cone structure; an outside of each of the slope surface structures 22-15 is provided with slots 22-18, the elastic rings 22-7 are arranged outside the clamping jaw set, and each of elastic rings 22-7 is sleeved in the corresponding slots 22-18 located at outer sides of the clamping jaws of the clamping jaw set. When the control terminal 22-14 moves upward along an axis of a clamping jaw control shaft 22-3, the control terminal 22-14 overcomes the force of the elastic rings 22-7, making the circular truncated cone structure of the clamping jaw set gradually change to the cylindrical structure, at the same time, each clamping jaw rotates with the help of the mounting pivot 22-10, making a clamping size of the clamping jaw set become smaller. Each clamping jaw is provided with a clamping plate 22-8 at the other end (i.e., the other end of the clamping jaw, where the mounting pivot 22-10 is located relative to the slope surface structure 22-15), during the rotation of the clamping jaws, the clamping plates 22-8 in the clamping jaw set performs opening and closing movement, and the clamping plates 22-8 drive, in cooperation with the rotation of the cap twisting main shaft 22-11, the Cell Factory cap or the centrifugal bottle cap to be unscrewed or screwed.

In order to adjust the change of the height of the clamping jaw set during the cap twisting process, the other end of the shaft sleeve for mounting clamping jaw 22-13 is provided with a buffer element 22-6. The buffer element 22-6 is arranged at the other end of the shaft sleeve for mounting clamping jaw 22-13, and is used to compensate for a distance difference between the shaft sleeve for mounting clamping jaw 22-13 and the cap twisting main shaft 22-11 during the rotation of the cap twisting main shaft 22-11. The buffer element 22-6 employs a spring, one end of which is connected to the shaft sleeve for mounting clamping jaw 22-13 (for example, a positioning device 22-12 is used, such as a lug boss 22-17 having a through-hole) and the other end is fixed to a platform. The platform is used for mounting of both the cap twisting main shaft 22-11 and the clamping jaw control shaft 22-3, i.e. the above support plate 22-5; or the platform is any plane above the shaft sleeve for mounting clamping jaw 22-13.

The clamping jaw control mechanism includes the clamping jaw control shaft 22-3 coaxially arranged with the cap twisting main shaft 22-11, and the clamping jaw control shaft is allowed to move along its own axial direction. The control terminal 22-14 is arranged at the end of the clamping jaw control shaft 22-3, the control terminal 22-14 is located in the cavity approximate to the circular truncated cone, in a case that a position of the control terminal 22-14 with respect to the cavity approximate to the circular truncated cone is changed, a rotation angle of the mounting pivot 22-10 of the clamping jaw is changed, and an opening degree of the clamping jaw set is also changed.

The liquid removing device includes a liquid removing needle 22-21, a liquid removing pipe, a liquid removing peristaltic pump 22-23 and a waste liquid reservoir which are sequentially in communication with each other, to remove the liquid in the cell storage container. For convenience or space saving, the waste liquid reservoir employs the waste liquid collection device on the liquid storage table. In a working passage or the washing passage, the liquid removing pipe is in communication with the discharge pipeline on the liquid storage table via the liquid removing peristaltic pump 22-23, to discharge the waste liquid into the waste liquid collection device. When the overall communication is realized, the liquid removing peristaltic pump 22-23 and the peristaltic pump of the liquid storage table may be integrated into one piece.

The liquid adding device includes a liquid adding needle 22-22, a liquid adding pipe, a liquid adding peristaltic pump 22-19 and a liquid storage device which are sequentially in communication with each other, to add the culture medium into the cell storage container. When being used for cell culture, the culture medium is stored in the liquid storage device; and when being used for washing, a buffer solution is stored in the liquid storage device.

The weighing platform is used for weighing the cell storage container, and its structure mainly adopts the weighing structure of the conventional technology, which is only applied in this application without improvement, and does not affect the understanding of the technical solution of this application by the person skilled in the art.

In order to facilitate practical application, main bodies of the cap twisting device, the liquid removing device and the liquid adding device are supported by a bracket. The liquid adding peristaltic pump 22-19, the liquid storage device, the liquid removing peristaltic pump 22-23, and the waste liquid reservoir are placed in an operation cabinet under the platform. In order to facilitate the operation of the mechanical arm for liquid adding or removing, the operation cabinet is provided with a telescopic drawer, and the waste liquid reservoir and the liquid storage device are placed in the telescopic drawer.

As a transmission mechanism, the cap twisting main shaft 22-11 and the clamping jaw control shaft 22-3 are coaxially arranged, that is, a diameter of the clamping jaw control shaft 22-3 is smaller than that of the cap twisting main shaft 22-11, and the clamping jaw control shaft 22-3 is arranged inside (runs through) the cap twisting main shaft 22-11. The cap twisting main shaft 22-11 only performs rotation around its own axis, and the clamping jaw control shaft 22-3 only performs linear movement along its own axis. In order to ensure the stability of the above two shafts in their respective independent movements (e.g. to reduce the wobble amplitude of the clamping jaw control shaft 22-3 during the telescopic movement along its own axis; and also to increase the choices of diversified raw materials in the production of the clamping jaw control shaft 22-3); and also to increase the service life of the above two shafts (e.g. the deviation of cap twisting caused by uncoaxiality due to frictional wear during long-term use). A shaft sleeve is provided between the clamping jaw control shaft 22-3 and the cap twisting main shaft 22-11, that is, the shaft sleeve effectively ensures the coaxiality between the clamping jaw control shaft 22-3 and the cap twisting main shaft 22-11, and the relative degree of freedom between the two shafts.

Preferably, a sterilization device is provided according to the present invention. As shown in FIG. 12, the sterilization device includes a sterilization pipeline and a sterilization source 22-20. The sterilization source 22-20 is communicated at an inlet of the liquid adding peristaltic pump 22-19, the sterilization pipeline has one end in communication with the liquid adding needle 22-22 and the other end in communication with the liquid removing needle 22-21. In order to simplify the overall structure and to facilitate automatic operation, the sterilization pipeline is supported by a rotating bracket, the rotating bracket has a first limit position at which the sterilization pipeline can be controlled to be parallel to the liquid adding needle 22-22, or the sterilization pipeline can be controlled to be parallel to the liquid removing needle 22-21; and the rotating bracket has a second limit position which ensures that the sterilization pipeline has one end connected to the liquid adding needle 22-22 and the other end connected to the liquid removing needle 22-21. In order to ensure that the sterilization passage 22-16 is completely closed during sterilization, at least one annular sealing ring is provided on each of the liquid removing needle 22-21 and the liquid adding needle 22-22.

As shown in FIG. 13, in order to ensure that the liquid in the liquid storage device connected to the liquid adding pump can be used up, the liquid storage device includes a liquid storage tank 22-24 and a liquid storage bag located in the liquid storage tank 22-24. The liquid storage tank 22-24 is provided with a through hole, the liquid storage bag is provided with a liquid outlet joint at the bottom, and the liquid outlet joint passes the through hole to be connected to the liquid adding pipe. The liquid storage tank is provided with a sloping surface 22-25, and a liquid storage bag fixing portion 22-26 is arranged at the top of the sloping surface 22-25. When being applied, the top of the liquid storage bag is fixed at the liquid storage bag fixing portion 22-26, the liquid storage bag is supported by the sloping surface 22-25, and the bottom of the liquid storage bag is overhung. In order to reduce costs, the sloping surface 22-25 employs a grid structure, that is, the sloping surface structure is formed by a plurality of transverse rods interlaced with a plurality of longitudinal rods.

Preferably, in this application, the cap twisting device, liquid adding device and liquid removing device work independently in the non-sterilized state, so in practical application, two or more groups may be used as required to realize cap twisting, liquid adding and liquid removing of multiple cell storage containers simultaneously.

The liquid storage table, the Cell Factory liquid exchange device and the centrifuge bottle liquid exchange device may work independently (each module works independently), or may be communicated to each other for washing, or may be communicated to each other for sterilization.

When being used in sterilization for the Cell Factory, washing should be performed before sterilization, and the communication manner is as follows.

In a case that the Cell Factory liquid adding device is in communication with the Cell Factory liquid storage device, the buffer solution is stored in the Cell Factory liquid storage device, the sterilization pipeline of the Cell Factory liquid exchange device is in communication with the Cell Factory liquid adding device and the Cell Factory liquid removing device, and the Cell Factory liquid removing device is in communication with the discharge pipeline of the waste liquid collection device via the liquid removing pipe, thus a washing passage of the Cell Factory liquid exchange device is formed. In a case that the Cell Factory liquid adding device is in communication with an outside high-temperature sterilization source, the sterilization pipeline of the Cell Factory liquid exchange device is in communication with the Cell Factory liquid adding device and the Cell Factory liquid removing device, the liquid removing pipe of the Cell Factory liquid removing device is in communication with the sterilization pipeline of the liquid storage table via the pipeline switching device, and the sterilization pipeline of the liquid storage table is in communication with an external sterilization condensing pipeline, thus a sterilization passage of the Cell Factory liquid exchange device is formed.

When being used in sterilization for the liquid storage table, the Cell Factory liquid exchange device and the centrifugal bottle liquid exchange device, washing should be performed before sterilization, and the communication manner is as follows.

In a case that the centrifuge bottle liquid adding device is in communication with the centrifuge bottle liquid storage device, the buffer solution is stored in the centrifuge bottle liquid storage device, the sterilization pipeline of the centrifuge bottle liquid exchange device is in communication with the centrifuge bottle liquid adding device and the centrifuge bottle liquid removing device, and the centrifuge bottle liquid removing device is in communication with the discharge pipeline of the waste liquid collection device via the liquid removing pipe, thus a washing passage of the centrifuge bottle liquid exchange device is formed. In a case that the Cell Factory liquid adding device is in communication with the external high-temperature sterilization source, the sterilization pipeline of the Cell Factory liquid exchange device is in communication with Cell Factory liquid adding device and the Cell Factory liquid removing device, the Cell Factory liquid removing device is in communication with the sterilization pipeline of the liquid storage table via the pipe switching joint, the sterilization pipeline of the liquid storage table is in communication with the centrifuge bottle liquid adding device, the centrifuge bottle liquid adding device is in communication with the centrifuge bottle liquid removing device via the sterilization pipeline of the centrifuge bottle liquid exchange device, and the centrifuge bottle liquid removing device is in communication with the external sterilization condensing pipeline, thus a combined sterilization passage is formed.

FIGS. 14 to 17 are schematic views showing the structure of a centrifuge, in some embodiments:

The operation region is provided with a full-automatic centrifuge in an integrated manner, the full-automatic centrifuge includes a drive mechanism and a rotation mechanism, the drive mechanism is configured to provide a driving force, and the rotation mechanism is configured to be driven by the driving force, to rotate around an axis of a drive shaft 23-2 of the drive mechanism.

As shown in FIG. 14, the drive mechanism includes a servo motor 23-1 provided with a zero-position switch 23-4, and an output shaft of the servo motor 23-1 is connected to the drive shaft 23-2.

The rotation mechanism includes a horizontal rotor 23-3 configured to rotate around the axis of the drive shaft 23-2. The horizontal rotor 23-3 has a plurality of arms of force extending in a radial direction by taking any point at the axis as a starting point. An end of the each of the plurality of arms of force is provided with a first arm of force component 23-3-1 and a second arm of force component 23-3-2, and a clamping portion is formed by the first arm of force component 23-3-1 of an end of one of the plurality of arms of force and the second arm of force component 23-3-2 of an end of an arm of force adjacent to the one of the plurality of arms of force. An included angle of the clamping portion preferably is 30°, 450 or 60°, correspondingly, the number of swinging buckets 23-5 that can be centrifuged are 12, 8 or 6. The included angle may be set to make the number of the arm of force be an even number, which is convenient for the centrifuging in a special case that the swinging buckets 23-5 are not full-loaded, for example, in a special situation that only two centrifuge containers 23-6 are used for centrifuging. Each of the swinging buckets 23-5 includes an annular wall and a bottom wall obliquely extending along a direction of the axis by taking a bottom circle of the annular wall as a starting point, and an upper end of the annular wall is mounted at the clamping portion. The annular wall is mainly used to limit the centrifuge container 23-6, and the bottom wall is used to support the centrifuge container 23-6.

In order to make it convenient for the mechanical arm to identify the presence of the centrifuge bottle in the swinging bucket 23-5, specifically, as shown in FIG. 16, the centrifuge is further provided with optical fiber detection switches arranged to surround the swinging buckets 23-5 in one-to-one correspondence. Each of the optical fiber detection switches 23-7 includes a signal emission unit configured to emit a signal 23-8 in a direction parallel to a plane where the rotation mechanism is located, and a signal reception unit configured to receive the signal which is reflected. The main principle is to use the linear transmission of the signal, and the difference of the light signal obtained at the reception site after reflection, refraction and scattering of the signal to detect the presence of the centrifuge bottle in the swinging basket 23-5. The signal can pass through the middle of the centrifuge bottle (in this case, the swinging basket 23-5 is correspondingly provided with a hole for the signal to pass through); or the signal can pass through the bottom of the centrifuge bottle.

As shown in FIGS. 15 and 16, to alleviate the vibration of the centrifuge, the rotating mechanism is supported by a buffer plate 23-10. Besides, to detect the vibration of the centrifuge, the horizontal rotor is placed in an annular inner cover 23-12, the annular inner cover 23-12 is mounted on the buffer plate, and the annular inner cover 23-12 is provided with a signal hole in the path of the signal, when the centrifuge vibrates abnormally (signal is reflected by the annular inner cover), the signal acquired by the optical fiber detection switch 23-7 is an abnormal signal.

To solve the problem of overheating of the centrifuge, in this embodiment, an emergency braking mechanism is added to the above technical solution of the centrifuge. As shown in FIG. 17, the emergency braking mechanism includes a spiral body made of a shape memory alloy with a two way memory effect and an emergency braking button arranged on the servo motor 23-1. The spiral body has an annular heated body 23-11 formed by a spiral action, and the annular heated body 23-11 has two extension ends with flanges 23-14. A first state of the spiral body is that the annular heated body is in a clearance fit with the drive shaft 23-2, and a second state of the spiral body is that the annular heated body is attached to a surface of the drive shaft 23-2. When the spiral body is in the second state, the extension ends turn on the emergency braking button by the flanges; and when the spiral body is in the first state, the flanges 23-14 have a set distance from the emergency braking button. The emergency braking button controls an input power connected to the servo motor 23-1, and when the spiral body is in the second state, the flanges 23-14 turns on the emergency braking button, to achieve emergency braking of the servo motor 23-1. The design of this embodiment effectively avoids the harm to cell culture caused by overheating after centrifuge failure or continuous long time of operation, and the most reasonable phase change temperature of the annular heated body can be obtained through theoretical design and limited times of test verification. The design of the specific shape memory alloy material with two ways memory effect according to the phase change temperature can be realized through the research on shape memory alloy in the conventional technology, which will not described in detail in this application.

In some embodiments, as shown in FIGS. 18 to 29, the operation region further includes an automatic cryogenic vial opening and aliquoting device, which is illustrated in detail as follows. The automatic cryogenic vial opening and aliquoting device includes a translation module 24-3, lifting module for cap screwing 24-41, and lifting module for liquid adding 24-71 mounted on the support platform 24-1.

The translation module 24-3 includes a base plate 24-36, a base plate slideway 24-31, a pallet slider 24-32, a first tray pallet 24-33, a second tray pallet 24-34, a horizontal drive device and a robot gripper 24-35. The horizontal drive device is arranged below the base plate slideway 24-31, the horizontal drive device includes a serve motor and a screw rod for driving. The robot places the metal bath with the cryogenic vials on the translation module 24-3 by the robot gripper 24-3, multiple cryogenic vials are placed on the second tray pallet 24-34, and the first tray pallet 24-33 is used to place the unscrewed vial caps. The horizontal drive device is arranged in the electric control cabinet 24-2, including the 400-watt serve motor and a screw rod for driving.

One side of the horizontal drive device (screw rod) is connected to the pallet slider 24-32, to realize the horizontal movement of the pallet slider 24-32 on the base plate slideway 24-31. A cable interface at a lower end of the servo motor is connected to an actuator of the motor, the translation module 24-3 moves the metal bath with the cryogenic vials to a robot pick-and-place position, i.e., the position of the robot gripper 24-35, and the robot automatically passes out the cryogenic vials. Preferably, the first tray pallet 24-33, the second tray pallet 24-34 and the base plate 24-36 are each provided with a plurality of round openings each having a diameter corresponding to that of the cryogenic vials, so as to better place the cryogenic vials and play a fixing role. The further improvement is that one side of the pallet slider 24-32 corresponding to the second tray pallet 24-34 is provided with a plurality of cryogenic vial fixing shafts 24-37, each has a structure specifically having six arc-shaped axial surfaces for fixing, and the transverse axial surface is circular-shaped, to form a bottom protection shaft from the bottom up for the corresponding cryogenic vial, which can further protect play the cryogenic vials.

The cryogenic vials are horizontally moved into the cap screwing main shaft 24-4 by the translation module 24-3 to get ready for cap screwing, and the cap screwing method is specifically realized as follows. The fixing platform includes a vial cap detection device 24-42, a vial body detection device 24-43, a cap screwing servo motor 24-44 and a vial cap detaching device 24-45. The vial cap detection device 24-42 is embodied as a reflective fiber optic sensor, and multiple reflective fiber optic sensors may be provided. In this embodiment, the number of the reflective fiber optic sensors is 10, so as to correspond to the figures. The reflective fiber optic sensors are 10 reflective laser sensors 24-512 arranged below the fixing platform and configured to detect a distance between the vial cap detaching device 24-45 and the vial cap. A laser pulse aiming at the vial cap is emitted by a laser emitting diode, and the distance between the vial cap detaching device 24-45 and the vial cap can be determined by recording and processing the elapsed time from the emitting to the and reception after return of the laser pulse. The principle of the vial body detection device 24-43 is the same, a single reflective fiber optic sensor is arranged, when the scattered light is not in a straight line, indicating that a cryogenic vial is brought to an upper position by the vial cap detaching device 24-45, that is, a group of vial bodies are not in the straight line.

The lifting module for cap screwing 24-41 includes a guide rail 24-401, a slider 24-402, and a motor 24-403 and a screw rod for driving, the motor 24-403 is arranged on the guide rail 24-401, an output end of the motor 24-403 is connected to the slider 24-402; the guide rail 24-401, the slider 24-402 and the fixing platform are arranged in a mutually parallel connection manner. The fixing platform is able to move up and down along the guide rail 24-401 under the driving of the motor 24-403, and the vial cap detaching device 24-45 can be moved to the position of the vial cap of the cryogenic vial according to actual operation choice.

A group of ten cap screwing servo motors 24-44 are arranged according to this embodiment, and are respectively connected to the vial cap detaching device 24-45. The cap screwing servo motor 24-44 employs a 50-watt servo motor. The vial cap detaching device 24-45 is controllably connected to the cap screwing servo motor 24-44. The vial cap detaching device 24-45 includes a spring 24-451, a guide pipe 24-452 provided with L-shaped movement openings at two surfaces, a slider moving pipe 24-453 and a casing pipe mounting plate 24-454. The slider moving pipe 24-453 is provided with two circular protrusions 24-455, and the guide pipe 24-452 is arranged at an outer periphery of the slider moving pipe 24-453. A rotation shaft is arranged inside the slider moving pipe 24-453, the rotation shaft has one end connected to the vial cap and another end connected to the casing pipe mounting plate 24-454. When the vial cap is being opened, the cap screwing servo motor 24-44 works to drive the casing pipe mounting plate 24-454 and the rotation shaft inside the slider moving pipe 24-453 to perform forward rotation and upward lifting movement, i.e., the protrusions 24-455 on the slider moving pipe 24-453 performs L-shaped movement on the surface of the guide pipe 24-452, which is in line with the path of the L-shaped movement opening, to perform forward rotation and upward lifting movement, and an inner side of a lower end of the guide pipe 24-452 is provided with threads engaged with the vial cap, thus the action of opening the vial cap is realized. The spring 24-451 is sleeved on an outer periphery of the guide pipe 24-452 in a snap-in manner, and the snap-in position on the guide pipe 24-452 is provided in a manner that hollow parts and solid parts are alternatively arranged at intervals, which not only realizes a stable snap-in structure of the spring 24-451 and the guide pipe 24-452, but also realizes securing the vial cap because part of the spring 24-451 itself is in contact with the vial cap. When the vial cap is being screwed, the path is reversed, the cap screwing servo motor 24-44 works to drive the casing pipe mounting plate 24-454 and the rotation shaft inside the slider moving pipe 24-453 to perform downward and reversed rotation movement, i.e., the protrusions 24-455 on the slider moving pipe 24-453 performs reversed L-shaped movement on the surface of the guide pipe 24-452, which is in line with the path of the L-shaped movement opening, to perform downward and reversed rotation movement, and thus the screwing of the vial cap is completed.

The guide pipe 24-452, slider moving pipe 24-453 and vial cap detaching device 24-45 as a whole are arranged in a detachable manner, i.e., the guide pipe 24-452 and slider moving pipe 24-453 are replaceable and can be specifically set according to the shape and structure of the cryogenic vial cap. Generally, the cryogenic vial cap is a circular edge with threads, or the cryogenic vial cap is polygonal. When the cryogenic vial cap is a circular edge with threads, a lower end of the vial cap detaching device 24-45 is provided with a circular cap opening structure matching the vial cap (which is specifically the present embodiment); however, when the cryogenic vial cap is polygonal, the lower end of the vial cap detaching device 24-45 is provided with a polygonal slider moving pipe 24-453 matching the vial cap, and the outer periphery of the polygonal slider moving pipe 24-453 is provided with a circular guide pipe 24-452 pressing device, the polygonal slider moving pipe 24-453 clamps the corresponding cryogenic vial cap, and the guide pipe 24-452 pressing device supplies an inward pressing force to realize the cap screwing. The polygonal slider moving pipe 24-453 matches the shape of the cryogenic vial cap and thus playing the role of grasping and fixing. Therefore, it is necessary to correspondingly set the vial cap detaching device 24-45 according to the cryogenic vial cap, and the arrangement is in a moveable connection manner, which is detachable and replaceable, and has a wider applicable range.

After opening the vial cap, liquid should be added into the cryogenic vial. The liquid adding device 24-5 includes a liquid adding platform 24-51, a sterilization platform 24-52 and a centrifuge bottle weighing platform 24-53. An upper end of the centrifuge bottle weighing platform 24-53 is provided with a centrifuge bottle placing table 24-54, which is used to place the centrifuge bottle. The centrifuge bottle weighing platform 24-53 is arranged at a lowermost end of the liquid adding device, and the centrifuge bottle weighing platform 24-53 is equipped with a weighing sensor and an FD-3 weighing module. The centrifuge bottle weighing platform 24-53 is used to weigh the liquid in the centrifuge bottle, to determine the weight of the liquid after the weight of the bottle is removed. In this embodiment, the weight of the liquid in the centrifuge bottle after the weight of the bottle is removed is 450 ml, which is not limited to this, the liquid is then evenly aliquoted in the cryogenic vials. A liquid removing double-needle 24-55 is embodied as one-piece, which can be placed on the liquid adding platform 24-51 or the sterilization platform 24-52 respectively, and the position is switched by the robot. As specifically shown in FIG. 31, upper and lower ends of the liquid removing double-needle 24-55 are hollow needles, and the position of the liquid removing double-needle 24-55 is switched between the liquid adding platform 24-51 and the sterilization platform 24-52 by the robot. The sterilization platform 24-52 is provided with a pushrod locking device 24-56, which is able to perform radial movement, i.e., one end is fixed and the other end is able to rotate. The pushrod locking device 24-56 is provided with a fitting opening, which is set in a circular shape, and is specifically corresponding to the circular structure of the liquid removing double-needle 24-55. When the fitting opening is rotated to a periphery of the liquid removing double-needle 24-55, the pushrod locking function can be realized, to make the liquid removing double-needle 24-55 be located at the sterilization platform 24-52, and to be fixed with the upper structure of the liquid removing double-needle 24-55 in a snap-in manner; besides, an upright post at a rear side of the liquid removing double-needle 24-55 is fixed, so that the structure is stable when the position is switched. The liquid adding platform 24-51 and the sterilization platform 24-52 are each provided with a laser sensor 24-512 for detecting the needle position of liquid removing double-needle 24-55.

The lifting module for liquid adding 24-71 and the translation module for liquid adding 24-72 are driven by a motor 24-403 and a screw rod. The translation module for liquid adding 24-72 is connected to the lifting module for liquid adding 24-71 through a sliding plate, and the translation module for liquid adding 24-72 is able to move on the lifting module for liquid adding 24-71 through the guide rail 24-401 and the sliding plate. A liquid adding needle 24-74 is arranged at a basic plate 24-73, the basic plate 24-73 is arranged on the translation module for liquid adding 24-72, the basic plate 24-73 is provided with a moving block, and the moving block is arranged to correspond to the guide rail 24-401 on the translation module for liquid adding 24-72. The lifting module for liquid adding 24-71 has two cable joints 24-75 connected to an actuator of the motor 24-403, to drive, under the driving of the motor 24-403, the liquid adding needle 24-74 on the basic plate 24-73 to perform up-down or front-back movement. A lower end of the liquid adding needle 24-74 is connected to a sterilization switching device 24-76, the sterilization switching device 24-76 includes two butting pipes 24-761 and an outlet pipe 24-762, the butting pipes 24-761 are configured to be connected to the liquid adding needle 24-74, the outlet pipe 24-762 may be understood as a check valve, and the outlet pipe has an upper end in communication with the butting pipes 24-761 and an opened side end. The liquid removing peristaltic pump 24-6 is provided with multiple pump heads provided with hoses correspondingly, and is connected to the liquid removing double-needle 24-55 on the liquid adding platform 24-51 and the liquid adding needle 24-74 on the liquid adding main shaft 24-7 through the hoses respectively. A sealing ring is sleeved on an outer shaft of the liquid adding needle 24-74, which plays the role of sealing when being connected to the hose; similarly, the sealing effect is good in butting connection, which prevents steam leakage.

During liquid adding, the liquid removing double-needle 24-55 on the liquid adding platform 24-51 is connected to the liquid removing peristaltic pump 24-6 through the hose, and then the liquid removing peristaltic pump 24-6 is connected to the liquid adding needle 24-74 on the liquid adding needle 24-7 through the hose. Upper and lower ends of the liquid adding needle 24-74 are hollow and communicated, one side of the needle is connected to the liquid removing peristaltic pump 24-6 through the hose, and the other side is connected to the cryogenic vial. The liquid removing peristaltic pump 24-6 pumps a cryogenic solution from the centrifuge bottle into the cryogenic vial to complete liquid adding of the cryogenic vial. The cryogenic vial is then moved to a position below the cap screwing position, to screw on the cryogenic vial cap.

During sterilization, the liquid removing double-needle 24-55 is first removed from the centrifuge bottle and switched to the sterilization platform 24-52. Steam for sterilization comes from a steam generator, flows to the liquid adding needle 24-74 through pipe connection, then reaches the sterilization switching device 24-76, and then flows from the butting pipes 24-761 to the outlet pipe 24-762, which forms a one-way passage. The above are only specific structures that can achieve the above functions, other structures not mentioned in the present invention that can achieve the same function are the equivalent replacement of the present invention.

The overall working process is as follows.

The robot places the set of cryogenic vials on the translation module 24-3, the translation module 24-3 moves to the position of the cap screwing main shaft 24-4 for cap screwing; the robot places the centrifuge bottle with liquid to be aliquoted on the centrifuge bottle placing table 24-54 of the liquid adding platform 24-51, then takes out the liquid removing double-needle 24-55 from the sterilization platform 24-52 and places it into the centrifuge bottle for cell freezing. The cap screwing main shaft 24-4 performs vial cap opening of a row of the cryogenic vials, then moves to the position of the liquid adding main shaft 24-7, and then the liquid removing peristaltic pump 24-6 pumps the cryogenic solution in the centrifuge bottle into the cryogenic vials, to complete liquid aliquoting for the row of the cryogenic vials. The structure combining the dual-needle and single-needle is employed, the dual-needle structure is used for liquid adding in the rapid liquid aliquoting at an early stage, and the single-needle structure is used for liquid adding at a later stage, which reduces liquid residual at the same time of ensuring the liquid adding efficiency. Then the cryogenic vials are moved to a position below the cap screwing main shaft 24-4, and the vial caps are screwed on the cryogenic vials. The opening-aliquoting-screwing process is repeated to complete the operation of all cryogenic vials, the translation module 24-3 moves the metal bath with cryogenic vials to the pick-and-place position of the robot, and the robot automatically passes out the cryogenic vials. The robot put the liquid removing double-needle 24-55 in the sterilization position for sterilization, the sterilization is performed at 121° C. for more than 20 minutes, and then the centrifuge bottle is taken out.

In Some Embodiments

Then the operation region is further provided with shakers in an integrated manner, and the shakers include a Cell Factory shaker and a centrifuge bottle shaker.

As shown in FIG. 31, the Cell Factory shaker includes an outer frame, where a shaking platform mounting area 25-11 and a drive mechanism mounted on the shaking platform mounting area 25-11 are laid on the outer frame; and a shaking platform configured to perform shaking under an action of the drive mechanism. The drive mechanism of the Cell Factory shaker includes a servo motor 25-12 and an eccentric shaft 25-13 connected to an output end of the servo motor 25-12, and the servo motor 25-12 is provided with a return-to-zero device; the shaking platform is arranged at a top end of the eccentric shaft 25-13; a surface of the shaking platform is provided with a Cell Factory clamping component, and a Cell Factory required to be shaken by the Cell Factory shaker are mounted at the Cell Factory clamping component through a Cell Factory support frame.

In order to avoid the secondary vibration caused by the vibration of the drive shaft during the shaking, the eccentric shaft 25-13 is further provided with a balancing plate 25-15. The balancing plate 25-15 is arranged in a direction opposite to the vibration direction of the shaking platform, to ensure the overall balance of the automatic shaker of the Cell Factory. Besides, for smooth shaking, four synchronous eccentric shafts 25-14 are provided, the four synchronous eccentric shafts 25-14 are arranged at four corners underneath the shaking platform and rotate synchronously with the drive shaft. The problem that the shaking platform cannot evenly shake during large area shaking is addressed, which effectively ensures the stability of the Cell Factory during the batch-type shaking, and at the same time ensures that the direction of the shaking platform unchanged during the shaking.

Particularly, an auxiliary mounting plate 25-16 is provided, the auxiliary mounting plate 25-16 is fixed on the outer frame, for example, the outer frame is provided with a mounting hole, and the auxiliary mounting plate 25-16 is supported by an edge of the mounting hole. The auxiliary mounting plate 25-16 is provided with a through hole for mounting the eccentric shaft 25-13. The servo motor 25-12 is suspended below the auxiliary mounting plate 25-16 by a bracket. The four synchronous eccentric shafts 25-14 each has one end mounted on the auxiliary mounting plate 25-16 by a bearing and the other end connected to the shaking platform.

From the above, according to the technical solution of the present invention, the servo motor 25-12 drives the eccentric shaft 25-13 to rotate through a shaft coupling, the eccentric shaft 25-13 drives the shaking platform to shake horizontally. The arrangement of the synchronous eccentric shafts 25-14 not only improves the load but also makes the shaking of the shaking platform smoother.

As shown in FIG. 30, the Cell Factory support frame has a Cell Factory placing box; where the Cell Factory placing box includes a bottom plate 25-1, a back plate 25-2, and two side plates 25-3. The bottom plate is partially sunken inward to form a Cell Factory limiting groove 25-4, and a sunken depth is between $1/100$ to $1/2$ of a height of the Cell Factory itself. A Cell Factory locking structure is provided, where the Cell Factory locking structure has a Cell Factory limiting element 25-5 and a Cell Factory locking element 25-6, one end of the Cell Factory limiting element 25-5 is mounted at an area of the back plate 25-2 corresponding to the Cell Factory limiting groove 25-4 in a manner that the Cell Factory limiting element 25-5 has one rotational degree of freedom, and one end of the Cell Factory locking element 25-6 is mounted at an area of the bottom plate 25-1 corresponding to the Cell Factory limiting groove 25-4 in a manner that the Cell Factory locking element 25-6 has one rotational degree of freedom; another end of the Cell Factory limiting element 25-5 and another end of the Cell Factory locking element 25-6 are allowed to be locked with each other, after being locked, the Cell Factory limiting element 25-5 is in parallel with the bottom plate 25-1, and the Cell Factory locking element 25-6 is in parallel with the back plate 25-2. Alternatively, the Cell Factory placing box includes a bottom plate 25-1, a back plate 25-2, and two side plates 25-3, where the bottom plate 25-1 is partially sunken inward to form a Cell Factory limiting groove 25-4. A Cell Factory locking structure is provided, where the Cell Factory locking structure has a Cell Factory limiting element 25-5 and a Cell Factory locking element 25-6, one end of the Cell Factory limiting element 25-5 is mounted at one of the two side plates 25-3 in a manner that in a manner that the Cell Factory limiting element 25-5 has one rotational degree of freedom, and one end of the Cell Factory locking element 25-6 is mounted at the other one of the two side plates 25-3 in a manner that the Cell Factory locking element 25-6 has one rotational degree of freedom; another end of the Cell Factory limiting element 25-5 and another end of the Cell Factory locking element 25-6 are allowed to be locked with each other, after being locked, the Cell Factory limiting element 25-5 is in parallel with the bottom plate 25-1.

Two sides of an upper end of the back plate are each provided with a positioning element 25-9, the bottom plate 25-1 is provided with a positioning hole at a corresponding width to match the positioning element 25-9, and a set distance is provided between the positioning hole and a joint between the back plate 25-2 and the bottom plate 25-1. In practical application, the set distance is generally not less than a distance between a Cell Factory cover and a Cell Factory edge. With the arrangement of the positioning hole, when the Cell Factory support frames are stacked in a vertical direction, there is misalignment between the adjacent two cell factories, to ensure that the Cell Factory cover can be exposed outside the Cell Factory support frame, so as to facilitate machine or manual operation. In other embodiments, multiple Cell Factory placing boxes may be provided in an integrated manner on one layer. Each of the Cell Factory placing boxes is provided with a Cell Factory locking structure.

Further, in order to realize stacking of the cell factories in the vertical direction without wobble between the Cell Factory support frames, an upper portion of the side plate 25-3 is provided with a first locking element 25-7 protruding beyond an upper surface of the side plate 25-3, a lower portion of the side plate 25-3 is provided with a second locking element 25-8 for locking the first locking element 25-7, and the second locking element 25-8 is misaligned with respect to the first locking element 25-7 by a set distance. When the Cell Factory support frames are being stacked, the positioning hole and the positioning element realize horizontal limitation, and the first locking element and the second locking element 25-8 realize double limitations in both the horizontal and vertical directions. In this case, it is required that the misalignment with the set distance between the second locking element 25-8 and the first locking element matches that the set distance between the positioning hole and the joint between the back plate 25-2 and the bottom plate 25-1.

As shown in FIG. 32, the centrifuge bottle shaker includes a shaking unit and a shaker base plate 26-2, and the shaking unit includes: a drive mechanism 26-1 for centrifuge bottle shaker, having an output shaft for outputting a rotating torque; a eccentric shake disk arranged at an output end of the output shaft in an eccentric manner and configured to rotate around an axis of the output shaft, the eccentric manner is defined that an axis of the eccentric shake disk is arranged in parallel with and in a preset distance from the axis of the output shaft; a centrifuge bottle clamp 26-3, where the centrifuge bottle clamp is arranged at the eccentric shake disk in a manner that the centrifuge bottle clamp has an elastic degree of freedom in an axial direction with respect to the eccentric shake disk, where the axial direction is defined as a direction in parallel with the axis of the output shaft.

Preferably, the number of the shaking unit is plural, the plurality of shaking units are uniformly arranged on the shaker base plate 26-2, the eccentric shake disk of each of the shaking units is mounted on a crankshaft via a bearing, and adjacent two eccentric shake disks are elastically connected with each other.

Particularly, the centrifuge bottle clamp 26-3 has a bottom seat 26-31, a centrifuge bottle support seat 26-32 and an elastic clamping element 26-33; where the centrifuge bottle support seat 26-32 is integrated at the bottom seat 26-31, and an upper surface of the centrifuge bottle support seat is partially sunken inward to form a bottom positioning portion matching a bottom of the centrifuge bottle; and the elastic clamping element 26-33 has a plurality of upright posts and at least one auxiliary ring 26-35, the plurality of upright posts each has one end fixed to the bottom seat 26-31 in a manner that the ends of the upright posts surrounds the centrifuge bottle support seat 26-32, to form a centrifuge bottle side clamping structure, the plurality of upright posts each has another end bent backward to form a reinforcing ring 26-34; and the auxiliary ring 26-35 surrounds all the upright posts and is connected to lower portions of all the upright posts.

The invention claimed is:

1. An automatic cell production line, comprising a culture region and an operation region; wherein the culture region is in B-level environment comprises a platform body, the platform body comprises a culture area, a refrigeration area and a robot equipped with a motion track; the motion track of the robot is arranged at a floor in a linear manner; the culture area and the refrigeration area are both located in an operation area of the robot;

the operation region is in A-level environment comprises a liquid storage table, a cell factory liquid exchange device, a centrifugal bottle liquid exchange device and a mechanical arm in an integrated manner; the liquid storage table, the cell factory liquid exchange device and the centrifugal bottle liquid exchange device are located within a control range of the mechanical arm;

a transfer window configured to transfer materials between the culture region and the operation region comprises a transfer turnplate and a transfer turnplate drive mechanism; the transfer turnplate has a zero position for the robot of the culture region to pick up and place the materials, and a working position for the mechanical arm of the operation region to pick up and place the materials; the transfer turnplate is configured to be driven by the transfer turnplate drive mechanism to rotate, to achieve switching between the zero position and the working position.

2. The automatic cell production line according to claim 1, wherein a waste liquid collection device and a pipe switching device are integrated at the liquid storage table;

a discharge pipeline and a sterilization pipeline of the waste liquid collection device are integrated at the waste liquid collection device;

the pipe switching device comprises a sterilization pipeline of the liquid storage table, and the sterilization pipeline of the liquid storage table is in communication with the sterilization pipeline of the waste liquid collection device; and a cell factory liquid storage device, a cell factory liquid removing device, a cell factory liquid adding device and a sterilization pipeline of the cell factory liquid exchange device are integrated at the cell factory liquid exchange device;

a centrifuge bottle liquid storage device, a centrifuge bottle liquid removing device, a centrifuge bottle liquid adding device, and a sterilization pipeline of the centrifuge bottle liquid exchange device are integrated at the centrifuge bottle liquid exchange device; and wherein in a case that the cell factory liquid adding device is in communication with the cell factory liquid storage device, a buffer solution is stored in the cell factory liquid storage device, the sterilization pipeline of the cell factory liquid exchange device is in communication with the cell factory liquid adding device and the cell factory liquid removing device, and the cell factory liquid removing device is in communication with the discharge pipeline of the waste liquid collection device via the discharge pipeline, to form a washing passage of the cell factory liquid exchange device;

in a case that the cell factory liquid adding device is in communication with an outside high-temperature sterilization source, the sterilization pipeline of the cell factory liquid exchange device is in communication with the cell factory liquid adding device and the cell factory liquid removing device, the cell factory liquid removing device is in communication with the sterilization pipeline of the waste liquid collection device, and the sterilization pipeline of the liquid storage table is in communication with an external sterilization condensing pipeline, to form a sterilization passage of the cell factory liquid exchange device;

in a case that the centrifuge bottle liquid adding device is in communication with the centrifuge bottle liquid storage device, a buffer solution is stored in the centrifuge bottle liquid storage device, the sterilization pipeline of the centrifuge bottle liquid exchange device is in communication with the centrifuge bottle liquid adding device and the centrifuge bottle liquid removing device, and the centrifuge bottle liquid removing device is in communication with the discharge pipeline of the waste liquid collection device, to form a washing passage of the centrifuge bottle liquid exchange device; and in a case that the cell factory liquid adding device is in communication with the external high-temperature sterilization source, the sterilization pipeline of the cell factory liquid exchange device is in communication with cell factory liquid adding device and the cell factory liquid removing device, the cell factory liquid removing device is in communication with the sterilization pipeline of the waste liquid collection device, the sterilization pipeline of the liquid storage table is in communication with the centrifuge bottle liquid adding device, the centrifuge bottle liquid adding device is in communication with the centrifuge bottle liquid removing device via the sterilization pipeline of the centrifuge bottle liquid exchange device, and the centrifuge bottle liquid removing device is in communication with the external sterilization condensing pipeline, to form a combined sterilization passage.

3. The automatic cell production line according to claim 2, wherein a sterilization pipeline locking structure is arranged at the liquid storage table, and the sterilization pipeline locking structure comprises a stepper motor and a rocker-slider structure; and wherein the rocker-slider structure comprises:

a slider, wherein the slider comprises a locking slot configured to lock the sterilization pipeline of the liquid storage table;

a slideway, wherein the slideway is configured to allow the slider to slide on along a preset route; and a two-bar linkage, wherein one end of the two-bar linkage is configured to be driven by the stepper motor, another end of the two-bar linkage is configured to drive, under driving of the stepper motor, the slider to slide along the slideway; and the sterilization pipeline of the liquid storage table is located on a motion path of the locking slot of the slider.

4. The automatic cell production line according to claim 2, wherein switching between the washing passage and the sterilization passage is performed by a pipeline switching device;

the pipeline switching device comprises an external support, and a switching device drive mechanism and a reversing mechanism both supported by the external support; wherein the external support is provided with a guide protrusion;

the switching device drive mechanism comprises a drive motor provided with a protruding element in a fixed manner, rotation output of the drive motor is performed by a gear shaft;

the reversing mechanism has a driven shaft, a pipe switching joint is fixed at a beginning end of the driven shaft through a bracket, and the bracket is allowed to rotate with respect to the driven shaft under an action of an external force; a follower disk, a gear disk and a guide rod are sequentially arranged at a shaft body section of the driven shaft; the follower disk is connected to the drive motor; the follower disk is located below the protruding element; the gear disk and the gear shaft are in gear transmission; an outer surface the guide rod is provided with a helical groove configured for the guide protrusion to slide in; a beginning end of the helical groove has a beginning horizontal segment, and a tail end of the helical groove has a tail horizontal segment.

5. The automatic cell production line according to claim 1, wherein the cell factory liquid exchange device and the centrifuge bottle liquid exchange device are provided with a cap twisting device in an integrated manner; and wherein the cap twisting device comprises a cap twisting mechanism and a clamping jaw control mechanism, and the cap twisting mechanism comprises:

a cap twisting main shaft configured to rotate around its own axis; and a clamping jaw set mounted at an end of the cap twisting main shaft, wherein the clamping jaw set comprises a clamping jaw limiting component and a plurality of clamping jaws; and wherein the clamping jaw limiting component comprises a plurality of elastic rings; each of the clamping jaws comprises a clamping portion, a mounting pivot connected to the cap twisting main shaft and a limiting structure arranged in sequence; the limiting structure corresponds to the cap twisting main shaft, one side of the limiting structure facing the cap twisting main shaft has a slope surface structure, and the slope surface structure is an inclined surface structure inclined toward the cap twisting main shaft; and the slope surface structures of the clamping jaws of the clamping jaw set together form a cavity approximate to a circular truncated cone; and wherein each of the plurality of elastic rings is sleeved on another side of the limiting structure of each of the plurality of clamping jaws of the clamping jaw set; the clamping jaw control mechanism comprises a clamping jaw control shaft coaxially arranged with the cap twisting main shaft, wherein the clamping jaw control shaft is allowed to move along its own axial direction; an end of the clamping jaw control shaft is provided with a control terminal, wherein the control terminal is located in the cavity approximate to the circular truncated cone, in a case that a position of the control terminal with respect to the cavity approximate to the circular truncated cone is changed, a rotation angle of the mounting pivot of the clamping jaw is changed, and an opening degree of the clamping jaw set is also changed.

6. The automatic cell production line according to claim 2, wherein the liquid storage table is further provided with a liquid storage bag shaking device and a liquid storage bag weighing device in an integrated manner, the liquid storage bag weighing device is located above the waste liquid collection device, and the liquid storage bag shaking device is located above the liquid storage bag weighing device; and wherein the liquid storage bag shaking device comprises a shaker drive mechanism and a storage bag box driven by the shaker drive mechanism and configured for storing a storage bag; the shaker drive mechanism and the storage bag box are drivably connected in a detachable manner.

7. The automatic cell production line according to claim 1, wherein the operation region is provided with a automatic centrifuge in an integrated manner, wherein the automatic centrifuge comprises a drive mechanism and a rotation mechanism, the drive mechanism is configured to provide a driving force, and the rotation mechanism is configured to be driven by the driving force, to rotate around an axis of a drive shaft of the drive mechanism; and wherein the rotation mechanism comprises:

a horizontal rotor configured to rotate around the axis of the drive shaft, and the horizontal rotor has a plurality of arms of force extending in a radial direction by taking the axis as a starting point; an end of each of the plurality of arms of force is provided with a first arm of force component and a second arm of force component, and a clamping portion is formed by the first arm of force component of an end of one of the plurality of arms of force and the second arm of force component of an end of an arm of force adjacent to the one of the plurality of arms of force;

a plurality of swinging buckets, wherein each of the swinging buckets comprises an annular wall and a bottom wall obliquely extending along a direction of the axis by taking a bottom circle of the annular wall as a starting point; and an upper end of the annular wall is mounted at the clamping portion; and the drive mechanism comprises a servo motor, the servo motor is provided with a zero-position switch, and an output shaft of the servo motor is connected to the drive shaft.

8. The automatic cell production line according to claim 7, wherein the automatic centrifuge further comprises a plurality of optical fiber detection switches arranged to surround the swinging buckets in one-to-one correspondence; wherein each of the optical fiber detection switches comprises a signal emission unit configured to emit a signal in a direction parallel to a plane where the rotation mechanism is located and a signal reception unit configured to receive the signal which is reflected; and wherein in a case that an emitted signal corresponds to the swinging bucket, the swinging bucket is provided with a hole in a signal traveling path of the optical fiber detection switch, and the signal reception unit is configured to receive the signal reflected by a wall of a centrifuge container or a wall of the swinging bucket; and in a case that the emitted signal passes below the swinging bucket, the signal reception unit is configured to receive the signal reflected by the wall of a centrifuge container or a wall of the drive shaft.

9. The automatic cell production line according to claim 1, wherein the operation region further comprises an automatic cryogenic vial opening and aliquoting device, the automatic cryogenic vial opening and aliquoting device comprises a cap screwing main shaft, cryogenic vial liquid adding device and cryogenic vial liquid adding main shaft, wherein the cryogenic vial liquid adding device and the cryogenic vial liquid adding main shaft are in communication with each other via a cryogenic vial liquid removing peristaltic pump when liquid adding is performed to a cryogenic vial;

the cap screwing main shaft comprises a lifting module for cap screwing and a fixing platform, wherein the lifting module for cap screwing comprises a guide rail, a slider and a motor, the slider is drivably connected to the motor and is configured to move along the guide rail, and the fixing platform is mounted at the slider and is allowed to move along with the slider;

a vial cap detection device, a vial body detection device, a cap screwing servo motor, and a vial cap detaching device are mounted on the fixing platform, wherein the vial cap detection device is embodied as a plurality of reflective laser sensors, the vial body detection device is a single reflective laser sensor, and the cap screwing servo motor is embodied as a set of a plurality of servo motors respectively connected to the vial cap detaching device;

the cryogenic vial liquid adding device comprises a cryogenic vial liquid adding platform, a sterilization platform and a centrifuge bottle weighing platform, wherein the cryogenic vial liquid adding platform and the sterilization platform are arranged in parallel, an upper end of the centrifuge bottle weighing platform is provided with a centrifuge bottle placing table, the cryogenic vial liquid adding platform or the sterilization platform is provided with a liquid removing double-needle, the sterilization platform is provided with a pushrod locking device, and the pushrod locking device is configured to move axially to be correspondingly clamped with an upper structure of the liquid removing double-needle, to achieve fixation;

the cryogenic vial liquid adding main shaft comprises a lifting module for liquid adding, a translation module for liquid adding, a basic plate and a liquid adding needle, wherein the liquid adding needle is fixed at the basic plate, the lifting module for liquid adding and the translation module for liquid adding are driven by a motor and a screw rod; the translation module for liquid adding is provided with a sliding plate, the lifting module for liquid adding is provided with a guide rail, and the translation module for liquid adding is allowed to move on the lifting module for liquid adding through cooperation between the sliding plate and the guide rail; and the basic plate is arranged at the translation module for liquid adding.

10. The automatic cell production line according to claim 9, wherein
the vial cap detaching device comprises a spring, a guide pipe provided with L-shaped movement openings at two surfaces, a slider moving pipe and a casing pipe mounting plate; wherein
an inner side of a lower end of the guide pipe is provided with threads configured to be engaged with a vial cap of the cryogenic vial, the guide pipe is arranged at an outer periphery of the slider moving pipe; the spring is sleeved at an outer periphery of the guide pipe in a clamped manner; and the two surfaces of the guide pipe provided with the L-shaped movement openings are opposite to each other;
the slider moving pipe is provided with two protrusions, and the protrusions are configured to move, under an action of a driving force, in the L-shaped movement openings in the surfaces of the guide pipe;
a rotation shaft is arranged inside the slider moving pipe, the rotation shaft has one end connected to the vial cap and another end connected to the casing pipe mounting plate; and
the casing pipe mounting plate is connected to the cap screwing servo motor; and wherein
in a case that the cap screwing servo motor drives, via the rotation shaft, the protrusions to perform L-shaped movement in a forward direction, the guide pipe drives the vial cap of the cryogenic vial to perform forward rotation and upward lifting movement, to unscrew the vial cap; and
in a case that the cap screwing servo motor drives, via the rotation shaft, the protrusions to perform L-shaped movement in a reversed direction, the guide pipe drives the vial cap of the cryogenic vial to perform downward and reversed rotation movement, to screw the vial cap.

11. The automatic cell production line according to claim 1, wherein
the operation region is further provided with shakers in an integrated manner, and the shakers comprise a cell factory shaker and a centrifuge bottle shaker; wherein
the cell factory shaker comprises an outer frame, a drive mechanism mounted on the outer frame, and a shaking platform configured to perform shaking under an action of the drive mechanism; the drive mechanism of the cell factory shaker comprises a servo motor and an eccentric shaft connected to an output end of the servo motor, and the servo motor is provided with a return-to-zero device; the shaking platform is arranged at a top end of the eccentric shaft; a surface of the shaking platform is provided with a cell factory clamping component, a cell factory required to be shaken by the cell factory shaker is mounted at the cell factory clamping component through a cell factory support frame;
the centrifuge bottle shaker comprises a shaking unit, and the shaking unit comprises:
a drive mechanism for centrifuge bottle shaker, having an output shaft for outputting a rotating torque;
an eccentric shake disk arranged at an output end of the output shaft in an eccentric manner and configured to rotate around an axis of the output shaft; the eccentric manner is defined that an axis of the eccentric shake disk is arranged in parallel with and in a preset distance from the axis of the output shaft;
a centrifuge bottle clamp, wherein the centrifuge bottle clamp is arranged at the eccentric shake disk in a manner that the centrifuge bottle clamp has an elastic degree of freedom in an axial direction with respect to the eccentric shake disk; the axial direction is a direction in parallel with the axis of the output shaft.

12. The automatic cell production line according to claim 11, wherein
the cell factory support frame has a cell factory placing box; and wherein
the cell factory placing box comprises:
a bottom plate, a back plate, and two side plates, wherein the bottom plate is partially sunken inward to form a cell factory limiting groove; and
a cell factory locking structure, wherein the cell factory locking structure has a cell factory limiting element and a cell factory locking element, one end of the cell factory limiting element is mounted at an area of the back plate corresponding to the cell factory limiting groove in a manner that the cell factory limiting element has one rotational degree of freedom, and one end of the cell factory locking element is mounted at an area of the bottom plate corresponding to the cell factory limiting groove in a manner that the cell factory locking element has one rotational degree of freedom; another end of the cell factory limiting element and another end of the cell factory locking element are allowed to be locked with each other, after being locked, the cell factory limiting element is in parallel with the bottom plate, and the cell factory locking element is in parallel with the back plate; or
the cell factory placing box comprises:
a bottom plate, a back plate, and two side plates, wherein the bottom plate is partially sunken inward to form a cell factory limiting groove; and
a cell factory locking structure, wherein the cell factory locking structure has a cell factory limiting element and a cell factory locking element, one end of the cell factory limiting element is mounted at one of the two side plates in a manner that the cell factory limiting element has one rotational degree of freedom, and one end of the cell factory locking element is mounted at the other one of the two side plates in a manner that the cell factory locking element has one rotational degree of freedom; another end of the cell factory limiting element and another end of the cell factory locking element are allowed to be locked with each other, after being locked, the cell factory limiting element is in parallel with the bottom plate.

13. The automatic cell production line according to claim 11, wherein
the number of the shaking unit is plural, the plurality of shaking units are uniformly arranged, the eccentric shake disk of each of the shaking units is mounted on a crankshaft via a bearing, and two adjacent eccentric shake disks are elastically connected with each other.

14. The automatic cell production line according to claim 11, wherein
the centrifuge bottle clamp has a bottom seat, a centrifuge bottle support seat and an elastic clamping element; wherein
the centrifuge bottle support seat is integrated at the bottom seat, and an upper surface of the centrifuge bottle support seat is partially sunken inward to form a bottom positioning portion matching a bottom of the centrifuge bottle; and the elastic clamping element has a plurality of upright posts and at least one auxiliary ring, the plurality of upright posts each has one end fixed to the bottom seat, the plurality of upright posts are arranged to surround the centrifuge bottle support seat to form a centrifuge bottle side clamping structure, the plurality of upright posts each has another end bent backward to form a reinforcing ring; the auxiliary ring surrounds all the upright posts and is connected to lower portions of all the upright posts.

* * * * *